United States Patent
Basta et al.

(10) Patent No.: US 9,047,747 B2
(45) Date of Patent: Jun. 2, 2015

(54) DUAL SERIAL BUS INTERFACE

(75) Inventors: Joseph Charles Basta, Duvall, WA (US); Robert Boyer Koenig, Redmond, WA (US); Joseph D. LaPerna, Redmond, WA (US); William Oren Wekell, Maple Valley, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 534 days.

(21) Appl. No.: 13/300,478

(22) Filed: Nov. 18, 2011

(65) Prior Publication Data

US 2012/0184120 A1    Jul. 19, 2012

Related U.S. Application Data

(60) Provisional application No. 61/415,799, filed on Nov. 19, 2010.

(51) Int. Cl.
| | | |
|---|---|---|
| *G06F 13/14* | (2006.01) | |
| *G08B 25/00* | (2006.01) | |
| *A61B 5/00* | (2006.01) | |
| *G06F 19/00* | (2011.01) | |
| *A61B 5/0205* | (2006.01) | |

(52) U.S. Cl.
CPC .............. *G08B 25/005* (2013.01); *A61B 5/0205* (2013.01); *A61B 5/746* (2013.01); *G06F 19/3418* (2013.01); *A61B 5/002* (2013.01)

(58) Field of Classification Search
USPC ......... 710/305–306, 110, 100, 105, 74; 700/3
See application file for complete search history.

(56) References Cited

U.S. PATENT DOCUMENTS

| 5,262,944 | A | | 11/1993 | Weisner | |
|---|---|---|---|---|---|
| 5,348,008 | A | | 9/1994 | Bornn | |
| 5,586,909 | A | * | 12/1996 | Saba | .............................. 439/559 |
| 5,787,298 | A | | 7/1998 | Broedner | |

(Continued)

FOREIGN PATENT DOCUMENTS

| WO | 9415523 | 7/1994 |
|---|---|---|
| WO | 9918705 | 4/1999 |
| WO | 2010126916 | 11/2010 |

OTHER PUBLICATIONS

International Search Report for PCT/US2011/61557, Apr. 23, 2012.

(Continued)

*Primary Examiner* — Tim Vo
*Assistant Examiner* — Kim T. Huynh
(74) *Attorney, Agent, or Firm* — Novel IP

(57) ABSTRACT

An interface protocol for patient monitoring systems includes a Dual Serial Bus (DSB) interface. The DSB interface includes a first serial protocol that is USB, Firewire, or Ethernet protocol and a second serial protocol that is a low power serial (LPS) protocol. DSB interfaces provide for communication between DSB Hosts and DSB Devices and allow for the transfer of operating and battery charging power from DSB Host to DSB Device. In addition, the DSB host contains a switched Auxiliary Voltage Supply (AVS) which can provide up to 15 W of power to DSB devices for battery charging or other high power needs. The DSB interface eliminates the need for multiple cables for different parameter sensing devices as there is only one type of connector and, accordingly, reduces the risk of damage caused by inadvertently plugging a parameter sensing device into the wrong receptacle.

14 Claims, 10 Drawing Sheets

(56) References Cited

U.S. PATENT DOCUMENTS

| | | | |
|---|---|---|---|
| 6,050,940 A | 4/2000 | Braun | |
| 6,674,837 B1 | 1/2004 | Taskar | |
| 6,735,648 B2 * | 5/2004 | Onishi | 710/62 |
| 7,024,569 B1 | 4/2006 | Wright | |
| RE39,233 E | 8/2006 | McGrath | |
| 7,751,878 B1 * | 7/2010 | Merkle et al. | 600/545 |
| 2002/0108011 A1 | 8/2002 | Tanha | |
| 2003/0130590 A1 | 7/2003 | Bui | |
| 2003/0171898 A1 | 9/2003 | Tarassenko | |
| 2004/0021705 A1 | 2/2004 | Baker | |
| 2004/0054261 A1 | 3/2004 | Kamataki | |
| 2004/0117209 A1 | 6/2004 | Brown | |
| 2004/0147818 A1 | 7/2004 | Levy | |
| 2004/0221077 A1 * | 11/2004 | Yen | 710/100 |
| 2005/0033124 A1 | 2/2005 | Kelly | |
| 2005/0059924 A1 | 3/2005 | Katz | |
| 2005/0065417 A1 | 3/2005 | Ali | |
| 2005/0146431 A1 | 7/2005 | Hastings | |
| 2005/0151640 A1 | 7/2005 | Hastings | |
| 2006/0199618 A1 | 9/2006 | Steer | |
| 2006/0258926 A1 | 11/2006 | Ali | |
| 2007/0032749 A1 | 2/2007 | Overall | |
| 2007/0060869 A1 | 3/2007 | Tolle | |
| 2007/0180140 A1 | 8/2007 | Welch | |
| 2007/0255116 A1 | 11/2007 | Mehta | |
| 2008/0039701 A1 | 2/2008 | Ali | |
| 2008/0177160 A1 | 7/2008 | Al Ali | |
| 2008/0177397 A1 * | 7/2008 | Davlin et al. | 700/3 |
| 2008/0281168 A1 | 11/2008 | Gibson | |
| 2009/0005703 A1 | 1/2009 | Fasciano | |
| 2009/0069642 A1 | 3/2009 | Gao | |
| 2009/0117784 A1 | 5/2009 | Wu | |
| 2009/0124239 A1 | 5/2009 | Tsuei | |
| 2009/0149901 A1 | 6/2009 | Jayne | |
| 2009/0182204 A1 | 7/2009 | Semler | |
| 2009/0192541 A1 | 7/2009 | Ortiz | |
| 2009/0193315 A1 * | 7/2009 | Gower et al. | 714/758 |
| 2010/0164452 A1 * | 7/2010 | Ruan et al. | 323/282 |
| 2010/0233891 A1 * | 9/2010 | Broeksteeg et al. | 439/63 |
| 2010/0238138 A1 | 9/2010 | Goertz | |
| 2010/0261979 A1 | 10/2010 | Kiani | |
| 2010/0298718 A1 | 11/2010 | Gilham | |
| 2010/0324380 A1 | 12/2010 | Perkins | |
| 2011/0152629 A1 | 6/2011 | Eaton | |
| 2011/0257489 A1 | 10/2011 | Banet | |
| 2011/0279383 A1 | 11/2011 | Wilson | |
| 2012/0075327 A1 | 3/2012 | MacKenzie | |

OTHER PUBLICATIONS

International Search Report for PCT/US2011/061554, Feb. 14, 2014.
International Search Report for PCT/US2011/061555, Apr. 17, 2012.
International Search Report for PCT/US2011/061558, Aug. 10, 2012.
International Preliminary Report on Patentability for PCT/US2011/061554, Feb. 25, 2014.

* cited by examiner

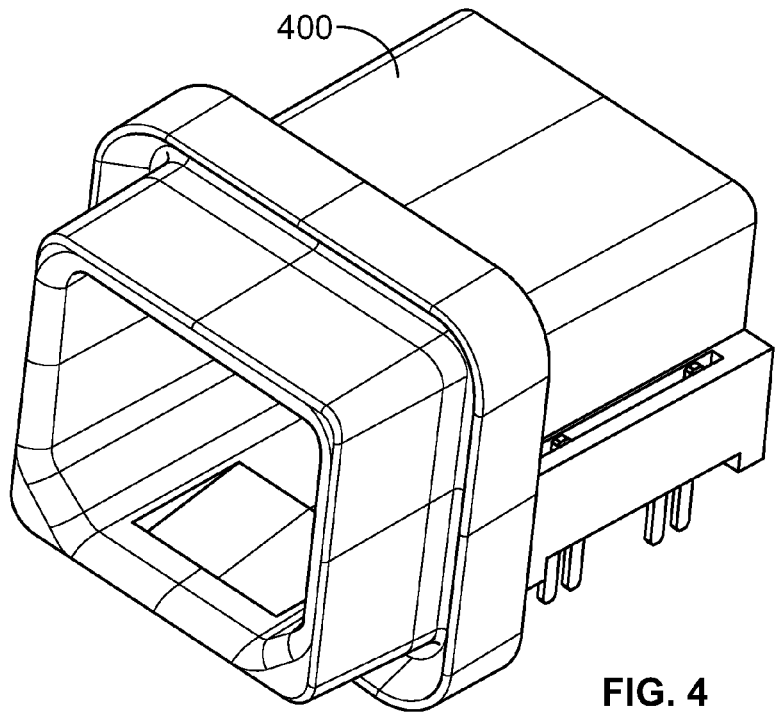

FIG. 4

| Series "A" Connectors | Series "B" Connectors |
|---|---|
| Series "A" Plugs are Always Oriented Upstream Toward the DSB Host System | Series "B" Plugs are Always Oriented Downstream Toward the DSB Device |
| 505 — [image of A plug] | [image of B plug] — 510 |
| The above Illustration is an "A" Plug (from the DSB Device). | The above Illustration is a "B" Plug (from the DSB Host System). |
| 515 — [image of A receptacle] | [image of B receptacle] — 520 |
| The above Illustration is an "A" Receptacle. Downstream Output from the DSB Host or Hub. | The above Illustration is a "B" Receptacle. UpStream Input to the DSB Device or Hub. |

FIG. 5A

DUAL SERIAL BUS INTERFACE

CROSS-REFERENCE TO RELATED APPLICATIONS

The present specification claims priority from U.S. Provisional Patent Application No. 61/415,799, entitled "Patient Monitoring System with Dual Serial Bus (DSB) Interface" and filed on Nov. 19, 2010, which is herein incorporated by reference in its entirety.

Co-pending U.S. patent application Ser. No. (to be determined), entitled "Self-Contained Patient Monitor", filed on Nov. 18, 2011 and assigned to the Applicant of the present invention, is also herein incorporated by reference in its entirety.

Co-pending U.S. patent application Ser. No. (to be determined), entitled "Configurable Patient Monitoring System", filed on Nov. 18, 2011 and assigned to the Applicant of the present invention, is also herein incorporated by reference in its entirety.

FIELD

This specification relates generally to hospital-based patient monitoring systems. More particularly, the present specification relates to the communication and power interfaces between specific components of patient monitoring systems, wherein the interfaces are achieved via a Dual Serial Bus (DSB) protocol, comprising a first protocol, such as USB, Firewire, or Ethernet protocol, and a second protocol, which is a Low Power Serial (LPS) protocol.

BACKGROUND

A patient monitoring system is an electronic medical device that measures a patient's various vital signs, collects and processes all measurements as data, and then displays the data graphically and/or numerically on a viewing screen. Graphical data is displayed continuously as data channels on a time axis (waveforms). Patient monitoring systems are positioned near hospital beds, typically in critical care units, where they continually monitor patient status via measuring devices attached to the patient and can be viewed by hospital personnel. Some patient monitoring systems can only be viewed on a local display, whereas others can be joined to a network and thereby display data at other locations, such as central monitoring or nurses' stations.

Portable patient monitoring systems are available for use by emergency medical services (EMS) personnel. These systems typically include a defibrillator along with the monitor. Other portable units, such as Holter monitors, are worn by patients for a particular time period and then returned to the physician for evaluation of the measured and collected data. Current patient monitoring systems are able to measure and display a variety of vital signs, including, pulse oximetry ($SpO_2$), electrocardiograph (ECG), invasive blood pressure (IBP), non-invasive blood pressure (NIBP), electroencephalograph (EEG), body temperature, cardiac output, capnography ($CO_2$), and respiration. Patient monitoring systems are capable of measuring and displaying maximum, minimum, and average values and frequencies, such as pulse and respiratory rates.

Data collected can be transmitted through fixed wire connections or wireless data communication. Power to patient monitoring systems can be supplied through a main power line or by batteries. While current patient monitoring systems are effective in monitoring patient conditions and notifying medical personnel of changes, they are not without certain drawbacks and limitations.

The Universal Serial Bus (USB) Interface is widely used in patient monitoring systems to connect a variety of sensors to the patient monitor. USB is a specification used to establish communication between peripheral devices and a host controller. With patient monitoring systems, the sensors are the peripheral devices and the monitor is the host controller. USB was originally designed for computers to replace serial and parallel ports and connectors, and its use has since expanded into a multitude of electronic applications. Systems using USB connections have an asymmetrical design, in which the host serves as a root hub and contains several downstream USB ports. Peripheral devices connect to the host via USB cables in a tiered star-shaped topography. Each peripheral device contains an upstream USB port. The USB cables connecting the host and peripheral devices have different connectors on the two ends. The proximal end connecting to the host has an upstream USB connector and the distal end connecting to a peripheral device has a downstream USB connector. The peripheral devices may also contain USB hubs, adding another tier to the system up to a maximum of five tiers, creating a tree-shaped topography. Peripheral devices may also draw power from the host via a USB connection. For the USB 2.0 specification, a hub can supply power in the range of 4.4 V to 5.25 V and up to 2.5 W per port. The many electronic components present in monitoring systems have varying power requirements. Some components are small with low power and/or are battery operated, and have very limited internal power capabilities. Other components require more power than what may be available from a standard USB port. Per the USB standard the device must provide the additional power itself. The power usage of the interface electronics for some devices can be a significant part of the component power.

Conventional sensor and monitor connectors are not without their drawbacks. In most legacy medical devices, each peripheral device has a unique connector controlled by a custom protocol, where the device cannot be plugged into the "wrong" connector. While some systems are moving towards USB-based cables and connectors, these connections are not without their drawbacks as well. The standard USB connection is designed to be used on a multitude of devices. Using this connector on a patient applied device could present a safety hazard if the patient applied device is connected to an inappropriate host device. Therefore, a need exists for a cable and connector interface system that incorporates the advantages of USB while eliminating the hazard mentioned above.

In addition, it is often necessary for components to receive more power than can be supplied by standard USB. Such components must then provide their own source of power at the expense of larger device size and complexity. Though power can be sent via a higher voltage auxiliary wire, the amount of this power is not unlimited. It is not uncommon for many devices to be connected to the same system, with each device competing for this limited power resource. Therefore, a need also exists for an auxiliary power system that includes a means for arbitrating and delivering power to the components so that the devices do not require individual power supplies and can thus remain small.

In the operating room and critical care units, some sensors monitoring vital signs need to be continuously connected to the patient. In such a case, patient movements are restricted due to environment conditions which may affect the sensor functionality. One such issue encountered in medical environments is liquid ingress, which can occur from a variety of sources, including but not limited to, blood splatter, liquid spill, and dropping small devices into water. This is a common scenario in many hospitals, resulting in system malfunction, time delay to restore functionality, and often damage to the system. Therefore, a need exists for a patient monitoring system in which the sensors and connectors are protected from liquid ingress.

SUMMARY

The present specification is directed toward a dual serial bus (DSB) communication and power interface system for electronic components, capable of operating in a first serial protocol and a second serial protocol, comprising a physical connection between said components, wherein said physical connection comprises: a first conductor, wherein said first conductor is a virtual bus (VBUS) conductor and transfers power from a first electronic component to a second electronic component; a second conductor, wherein said second conductor is a data transmitting conductor and sends data from said first electronic component to said second electronic component; a third conductor, wherein said third conductor is a data receiving conductor and receives data to said first electronic component sent from said second electronic component; a fourth conductor, wherein said fourth conductor is a ground (GND) conductor and receives return power to said first electronic component transferred from said second electronic component; a fifth conductor, wherein said fifth conductor is an auxiliary voltage supply (AVS) conductor and transfers higher amounts of power from said first electronic component to said second electronic component than is capable of being transferred by said first conductor; and, a sixth conductor, wherein said sixth conductor is a spare conductor.

In one embodiment, the dual serial bus communication and power interface system is used to communicate and distribute power between components of a patient monitoring system.

In one embodiment, each component of the dual serial bus communication and power interface system is designated as a dual serial bus (DSB) Host, DSB Device, or, both a DSB Host and DSB Device. In one embodiment, a DSB Host is in bi-directional communication with a connected DSB Device, can supply operating and battery charging power to the connected DSB Device, and can control the connected DSB Device.

In one embodiment, a DSB Host contains a switched Auxiliary Voltage Supply (AVS) which can provide up to 15 W of power to attached DSB Devices. In one embodiment, the AVS power must be requested by a DSB Device and granted by the DSB Host.

In one embodiment, a DSB Host comprises any one of a Patient Worn Hub (PWH), Smart Display (SD), Headless Display (HD), Network Computer (NC), or, Parameter Transceiver (PT). In one embodiment, a DSB Device comprises at least one of a ECG/respiration in 3-lead, 5-lead, 6-lead, and 10-lead configurations, $SpO_2$ sensor, invasive blood pressure (IBP) 4 channel adapter and single channel connection, cardiac output sensor, end tidal $CO_2$ sensor, continuous temperature sensor, $SvO_2$ sensor, bispectral index (BISx) sensor, multi-gas sensor, tympanic temperature sensor, or EEG sensor. In one embodiment, a Patient Worn Hub (PWH) functions both as a DSB Host and a DSB Device.

In one embodiment, each DSB Host contains at least one DSB-A type receptacle which accepts only a DSB-A type plug and/or at least one integrated cable with a DSB-B type plug at the end of said cable and, each DSB Device contains at least one DSB-B type receptacle which accepts only a DSB-B type plug and/or at least one integrated cable with a DSB-A type plug at the end of said cable. In one embodiment, each DSB-A type receptacle and DSB-B type receptacle comprises a double stage sealing over the receptacle socket outer surface to prevent liquid ingress at the point of connection.

In one embodiment, a DSB Device is docked directly with a DSB Host, connected to a DSB Host via a fixedly attached cable, or connected to a DSB Host via a detachable DSB cable, wherein each detachable DSB cable contains a DSB-A type plug on one end and a DSB-B type plug on the other end. In one embodiment, the fixedly attached cable and detachable DSB cable each transfer signal and power over a shielded multi-wire cable terminating in a connector with mating shields. In one embodiment, the VBUS voltage present on the DSB Host device determines whether the DSB Device operates in the USB mode or the LPS mode.

The present specification is also directed toward a dual serial bus communication and power interface between a first host and a first device, wherein said first host and first device transmit and receive data across a physical communication medium and wherein said first host and said first device communicate and/or provide or receive power through a first protocol and a second protocol, wherein said first protocol is at least one of a USB protocol, Firewire protocol, or Ethernet protocol, and wherein said second protocol provides power to said first device via a serial connection, wherein the power supplied to said first device by said second protocol is of a lower amount than power supplied by said first protocol.

In one embodiment, the power supplied by said first protocol is equal to 5 V and power supplied by said second protocol is equal to 3.3 V.

In one embodiment, the first host determines whether to provide power via said first or second protocol to said first device based upon power requirement need information sent to said first host by said first device upon connection of said first device to said first host.

The aforementioned and other embodiments of the present specification shall be described in greater depth in the drawings and detailed description provided below.

BRIEF DESCRIPTION OF THE DRAWINGS

These and other features and advantages will be further appreciated, as they become better understood by reference to the detailed description when considered in connection with the accompanying drawings:

FIG. 4 is a three-dimensional illustration of one embodiment of a DSB B connector of a patient monitoring system;

FIG. 5A depicts three-dimensional illustrations of the four types of connectors included in the DSB interface;

DETAILED DESCRIPTION

Figure 1:
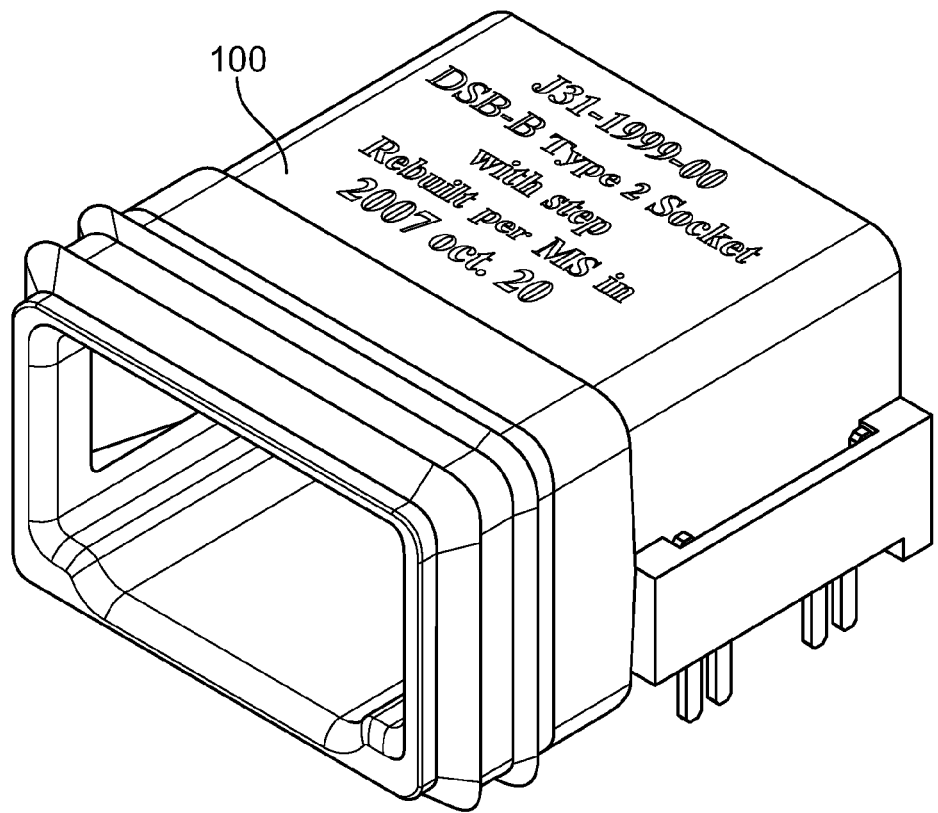
FIG. 1 is a three-dimensional illustration of one embodiment of a DSB A Connector of a patient monitoring system.

In one embodiment, the present specification is directed toward a patient monitoring system comprised of a plurality of non-integrated components including a display, a monitor, one or more modules, and at least one patient parameter measuring device. A variety of patient parameters can be monitored and the parameter measuring devices are connected to the system via Dual Serial Bus (DSB) connectors and DSB cables.

The patient monitoring system described in co-pending U.S. patent application Ser. No. (to be determined) entitled "Configurable Patient Monitoring System", filed on Nov. 18, 2011 and assigned to the Applicant of the present invention, and the Patient Worn Hub (PWH) of co-pending U.S. patent application Ser. No. (to be determined) entitled "Self-Contained Patient Monitor", filed on Nov. 18, 2011 and assigned to the Applicant of the present invention, are two exemplary systems that utilize the DSB interface. Both applications are hereby incorporated by reference.

The following terms and abbreviations are used throughout the specification: "Bridge" is used to define a serial device interface, which is an isolated interface to third party devices through their RS232 output. "DSB", as mentioned above, is a Dual Serial Bus, which is an interface that supports communication via both USB and LPS.

"FED" refers to a front end device, which is a device for collecting patient parameter data. "FEC" refers to a FED controller, which is a software driver that resides on a host that communicates with and controls a FED. "DSB Host" refers to a system device that controls the DSB interface, which can be a Patient Worn Hub (PWH) or Smart Display (SD), or a Parameter Transceiver (PT). "SD" refers to a Smart Display and is a patient monitor with an integrated display that acts as a DSB Host and runs the algorithms needed for patient parameter processing. An SD can extend the functionality of a Patient Worn Hub (PWH) and provides a larger local display. "HD" refers to a Headless Display and is equivalent to a Smart Display (SD) except that it uses an external display rather than having an integrated display.

"DSB Device" refers to a system device that is controlled by a DSB Host through a DSB interface, such as a FED or PWH. "ICD" is an interface control document, which defines the software protocols for the DSB. "LPS" means Low Power Serial. "NC" refers to network computer. "PWH" refers to Patient Worn Hub, which is a host that will run the programmatic processes needed for patient parameter processing, whereby the PWH may have several DSB Host interfaces. "PT" refers to a parameter transceiver, which is a small wireless transceiver that will send patient parameter data to a central system for processing. In one embodiment, the PT has two DSB Host interfaces.

"RS232 Serial Communication Interface" is the ANSI Standard EIA232. "SC" is a serial communication interface, which is a two-wire, asynchronous serial communication interface (TX, RX) that is similar to RS232 except at transistor-transistor logic (TTL) levels. "TP" is a telemetry processor, which is a computer system that will run ECG and respiratory parameter algorithms in a telemetry system. "USB" is a Universal Serial Bus.

As mentioned above, conventional sensor and monitor connectors are not without their drawbacks. In most legacy medical devices, each peripheral device has a unique connector controlled by a custom protocol, where the device cannot be plugged into the "wrong" connector. USB has the advantage of a single cable that may be used with any device. The cable ends are unique so that misconnections are not possible without considerable effort. The disadvantage to USB is that the connectors exist on a multitude of devices, particularly on devices not qualified for use in the patient vicinity. Connecting one of these non-qualified, unauthorized devices to a medical device could present significant shock hazard to the patient. Additionally, power available to run USB devices is limited to no more than 2.5 W per device and therefore may not be suitable for charging a device.

In one embodiment, the DSB interface solves these issues by creating a unique connector interface, with qualities similar to the USB connector, but which are unique to medical devices. Also incorporated in this connector is a method to provide up to an additional 15 W of auxiliary power to allow the DSB Device to operate without the need to provide a self-powered solution. Because it is possible to connect more devices than a particular host device may be capable of powering, the DSB interface also provides a mechanism wherein the device requests auxiliary power and the host only grants the request if sufficient capacity remains to support the request. In battery powered situations where run time needs to be optimized, a special low power serial protocol exists that does not use the USB infrastructure but utilizes a protocol optimized for this purpose and requiring very low power. Thus, the LPS portion of the DSB interface exists to address the problem of the interface electronics requiring more energy than the function of the device itself.

In one embodiment, the patient monitoring system of the present invention utilizes a novel interface between the monitor and the patient parameter devices, referred to as Dual Serial Bus (DSB) and comprising both DSB connectors and DSB cables to address the drawbacks inherent to conventional connectors, namely, connector mismatch, searching for the correct mating connector, maintaining an inventory of cables for different sensors, danger to the system and patient through incorrect usage, and power consumption issues which are all eliminated by utilizing the DSB system wherein no sensor is cable dependent. The DSB interface is a multifunctional interface that can provide communications, operating power, and battery charging capabilities. The DSB interface system, in one embodiment, provides a single cabling assembly which is independent of the sensing or monitoring device. In other words, there exists only one generic type of cable (DSB cable) that connects between components of the patient monitoring system disclosed herein, wherein its functionality is dictated by the components to which it is connected.

The specification describes the electrical characteristics, signal definitions, bus attributes, signaling speed, protocol architecture, and mechanical characteristics of the patient monitoring system interface of the present invention. The DSB interface is the primary patient monitoring system interface and is used to connect Hosts to Devices and connect devices like the Parameter Transceiver (PT) to a battery charger and the Patient Worn Hub (PWH) to the Smart Display (SD) or charging cradle. The following description also includes DSB interface performance specifications that provide the basis for the interface design and performance verification in one embodiment of the present invention. Specifications such as interface with other equipment, voltage and current supplied, power control, bus signal definitions, bus type control, etc., are also identified. Thus, in one embodiment, the DSB interface architecture provides a flexible interface for both proprietary and third party devices that are available now or may be available in the future.

The DSB interface comprises a first serial communication protocol and a second communication protocol. In one embodiment, the first protocol is the industry standard USB protocol. In another embodiment, the first protocol is FireWire. In another embodiment, the first protocol is Ethernet. In one embodiment, the second protocol is the Low Power Serial (LPS) protocol, a Spacelabs Healthcare® proprietary protocol, which is an asynchronous serial protocol similar to the type used in a typical RS232 port. In one embodiment, the DSB interface comprises six conductors which include the following: a virtual bus (VBUS) conductor for supplying power; two data conductors for data flow; a ground (GND) conductor; an auxiliary voltage supply (AVS) conductor to provide additional power for battery charging and higher power needs; and, a spare conductor for potential future use.

In one embodiment, the DSB provides a bidirectional serial communication interface and also provides power from a DSB Host to a DSB Device in the patient monitoring system of the present invention. Thus, a patient monitoring system component can have a DSB Host, a DSB device, or both. The DSB Host is the system control device and can be used to communicate with and/or control devices.

It should be appreciated that electronic communication between devices may be effectuated by the transmission and receipt of data between applications executing in any of the devices or computing systems. Each application is configured to receive, transmit, recognize, interpret, and process such request data and information. It should further be appreciated that both the system described herein have receivers and transmitters capable of sending and transmitting data, at least one processor capable of processing programmatic instructions, memory capable of storing programmatic instructions, and software comprised of a plurality of programmatic instructions for performing the processes described herein.

Software present on the DSB Host recognizes when a DSB Device is attached and determines the power requirements of the DSB Device. Once power requirements are determined, the DSB Host provides power to the DSB Device via the VBUS conductor, wherein the USB protocol provides 5 V to the DSB Device and the LPS protocol provides 3.3 V to the DSB Device. In one embodiment, the DSB Device requires battery charging or other higher power needs. In such a situation, the DSB Host provides 18 V of power via the AVS conductor to the DSB Device.

As mentioned above, in one embodiment, a system component is a DSB Host. In another embodiment, a system component is a DSB Device. In another embodiment, a system component is both a DSB Host and a DSB Device.

In one embodiment, the following components are identified as DSB hosts: Patient Worn Hub (PWH); Smart Display (SD); Headless Display (HD); Network Computer (NC); and, Parameter Transceiver (PT). One of ordinary skill in the art would appreciate that this list is exemplary and other components may function as DSB Hosts.

In one embodiment, the following components are identified as DSB devices (measure patient physiological parameters), also known as Front End Devices (FED's): ECG/Respiration in 3-lead, 5-lead, 6-lead, and 10-lead configurations; SpO$_2$ sensors from various providers, including proprietary and third party; invasive blood pressure (IBP) 4 channel adapter and single channel connection; cardiac output sensor/monitors, end tidal CO$_2$ sensor/monitors; continuous temperature sensors; SvO$_2$; bispectral index (BISx); multi-gas; tympanic temperature; and EEG. One of ordinary skill in the art would appreciate that this list is exemplary and other components may function as DSB Devices.

Table 1 lists system connections with pin designations included in the DSB Interface System of the present invention.

TABLE 1

| Mode/Class Example of Salish Component) | Connection | Type | Pin # TBD VBUS | Pin # TBD D+/ RX | Pin # TBD D−/ TX | Pin # TBD GND | Pin # TBD AVS (Auxiliary Voltage Supply) | Pin # TBD Spare | Shield Shield |
|---|---|---|---|---|---|---|---|---|---|
| USB Mode (SD/HD) | DSB A Receptacle | DSB Host | +5 V Power Output | D+ IO | D− IO | Common Return | +18 V Aux. Voltage Supply Out | TBD | EMI Shielding |
| | DSB B Plug | DSB Host | +5 V Power Output | D+ IO | D− IO | Common Return | +18 V Aux. Voltage Supply Out | TBD | EMI Shielding |
| USB Mode (PWH) | DSB A Receptacle | DSB Host | +5 V Power Output | D+ IO | D− IO | Common Return | +18 V Aux. Voltage Supply Out | TBD | EMI Shielding |
| | DSB B Plug | DSB Host | +5 V Power Output | D+ IO | D− IO | Common Return | +18 V Aux. Voltage Supply Out | TBD | EMI Shielding |
| | DSB B Receptacle | Device | +5 V Power Input | D+ IO | D− IO | Common | AVS In (PWH Charging Input) | TBD | EMI Shielding |
| LPS Mode (PT) | DSB A Receptacle | DSB Host (Device - to PT Charger) | +3.3 V Power Output | TX Out | RX In | Common Return | PT Charging Input | TBD | EMI Shielding |
| | DSB B Plug | DSB Host | +3.3 V Power Output | TX Out | RX In | Common Return | N/A | TBD | EMI Shielding |

TABLE 1-continued

System Connections

| Mode/Class Example of Salish Component) | Connection | Type | Pin # TBD VBUS | Pin # TBD D+/ RX | Pin # TBD D−/ TX | Pin # TBD GND | Pin # TBD AVS (Auxiliary Voltage Supply) | Pin # TBD Spare | Shield Shield |
|---|---|---|---|---|---|---|---|---|---|
| FED w/o cable | DSB B Receptacle | DSB Device | +5 V/+3.3 V Power Input | RX In | TX Out | Common | AVS In | TBD | EMI Shielding |
| FED cabled | DSB A Plug | DSB Device | +5 V/+3.3 V Power Input | RX In | TX Out | Common | AVS In | TBD | EMI Shielding |
| PT Charger | DSB A Plug | DSB Device | TBD | TX Out | RX In | Common Return | PT Charging Output | TBD | EMI Shielding |
| DSB Cable(s) | DSB-A Plug/ DSB-B Plug | Passive | Required | Req. | Req. | Required | As Required | As Req. | Req. |

The physical interface is embodied by an interconnect scheme that connects the Patient Worn Hub, Smart Display, Parameter Transceiver, FED's, and other components, which each define a class of devices. New device classes can be added to allow expansion and future growth. The interface has two ends, a DSB host and a DSB device. In one embodiment, a DSB host and a DSB device are connected directly to each other. Components that can be connected directly to each other are controlled by their physical shape and connector end type.

In one embodiment of the present invention, there are four different connector types in the DSB system and a set of associated rules. In one embodiment, in an effort to minimize end user termination problems, DSB, just like USB, uses a "keyed connector" protocol. There is a connector "A" type with receptacle and plug, and a connector "B" type with receptacle and plug. The physical difference in the Series "A" and "B" connectors insures proper end user connectivity. The "A" plug end will always and only connect to a host "A" receptacle. The "B" plug end will always and only connect to a device "B" receptacle. DSB-A is a unique connector set (plug and receptacle) on the DSB host end of the connection. DSB-B is a unique connector set (plug and receptacle) on the DSB device end of the connection. All DSB devices must have an attached Series "A" connector or a "B" connector that allows device connection using a standard detachable DSB cable. This facilitates end user cable replacement.

In one embodiment, as can be seen in Table 1 above, when in the USB mode, a Smart Display (SD) or Headless Display (HD) acts as a DSB Host and the connection includes a DSB A Receptacle and/or a DSB Plug. In one embodiment, six pins are included in the connection. The function of a first pin is Virtual Bus (VBUS) and provides 5 V power output. Second and third pins are used for data transfer and are designated D+ input/output (IO) and D− input/output (IO), respectively. A fourth pin functions as a ground (GND) or common return pin. A fifth pin functions as the Auxiliary Voltage Supply (AVS), which provides 18 V for battery charging or other high power needs. A sixth pin is reserved as a spare for possible future uses. The connection includes electromagnetic interference (EMI) shielding.

In one embodiment, when in the USB mode, a Patient Worn Hub (PWH) acts as a DSB Host and includes the features of the connection described above and, also acts as a DSB Device in which the associated connection includes a DSB B Receptacle. The pins share the same functions as those described above with the exception that the fifth pin receives the charging input from the AVS (input) when the PWH is acting as a DSB Device. A sixth pin is reserved as a spare for possible future uses. The connection includes electromagnetic interference (EMI) shielding.

In one embodiment, when in the Low Power Serial (LPS) mode, a Parameter Transceiver (PT) acts as a DSB Host and the connection includes a DSB A Receptacle and/or a DSB B Plug. The function of a first pin is Virtual Bus (VBUS) and, in LPS mode, provides 3.3 V power output. Second and third pins are used for data transfer and are designated transmitter TX(out) and receiver RX(in), respectively. A fourth pin is for GND or common return. When the PT is acting as a DSB Host, the fifth pin has no function. In one embodiment, it is possible for the PT to act as a DSB Device to a Parameter Transceiver (PT) Charger. When the PT is acting as a DSB Device, the fifth pin at the DSB A Receptacle receives the charging input from the PT Charger input. A sixth pin is reserved as a spare for possible future uses. The connection includes electromagnetic interference (EMI) shielding.

In one embodiment, a front end device (FED) that does not include an attached cable always acts as a DSB Device and only includes a DSB B Receptacle. A first VBUS pin receives either 5 V or 3.3 V power input. A second pin is used for data transfer and is designated RX(in) while a third pin is also used for data transfer and is designated TX(out). A fourth pin is for GND or common return. The fifth pin receives the charging input from the AVS(in). A sixth pin is reserved as a spare for possible future uses. The connection includes electromagnetic interference (EMI) shielding.

In one embodiment, a front end device (FED) that includes an integrated cable always acts as a DSB Device and only includes a DSB A Plug. A first, VBUS pin receives either 5 V or 3.3 V power input. A second pin is used for data transfer and is designated RX(in) while a third pin is also used for data transfer and is designated TX(out). A fourth pin is for GND or common return. The fifth pin receives the charging input from the AVS(in). A sixth pin is reserved as a spare for possible future uses. The connection includes electromagnetic interference (EMI) shielding.

In one embodiment, a PT Charger acts as a DSB Device and only includes a DSB Plug. A second pin is used for data transfer and is designated TX(out) while a third pin is also used for data transfer and is designated RX(in). A fourth pin is for GND or common return. The fifth pin provides charging output to the PT. A sixth pin is reserved as a spare for possible future uses. The connection includes electromagnetic interference (EMI) shielding.

In one embodiment, a DSB Cable acts passively and is neither a DSB Host or DSB Device, comprising both a DSB A Plug and a DSB B Plug. The first pin is required for VBUS. The second and third pins are required for data transfer. The fourth pin is required for GND or common return. The fifth and sixth pins are used as required by the attached DBS Host and DSB Device. EMI shielding is required in the DSB Cable.

Thus, the DSB interface of the present invention permits connecting the patient monitoring system components together. However, not all functions are available (or are needed) in all components. Table 2 includes various embodiments of the DSB Host/DSB Device compatibility and supported special functions.

connection, the DSB interface operates in the LPS mode and provides 3.3 V power output from the PT to the FED.

Additionally, the PT can act as a DSB Host to a FED with an integrated cable. The FED connects to the PT via a DSB A Plug present on the integrated cable and a DSB A Receptacle on the PT. In such a connection, the DSB interface operates in the LPS mode and provides 3.3 V power output from the PT to the FED.

TABLE 2

Exemplary DSB Component Connectivity Configurations

| | | DSB Host | | | |
|---|---|---|---|---|---|
| DSB Device | Connection | SD/HD DSB A Receptacle or DSB B Plug | PWH DSB A Receptacle or DSB B Plug | PT DSB A Receptacle or DSB B Plug | PT Charger DSB A Plug |
| PWH | DSB B Receptacle | USB Mode AVS capabilities | | NA | NA |
| PT | DSB A Receptacle | NA | NA | | LPS Mode Charging SW upgrade capabilities |
| FED (no cable) | DSB B Receptacle | USB Mode SW upgrade capabilities AVS capabilities | USB Mode SW upgrade capabilities AVS capabilities | LPS Mode | NA |
| FED (cabled) | DSB A Plug | USB Mode SW upgrade capabilities AVS capabilities | USB Mode SW upgrade capabilities AVS capabilities | LPS Mode | NA |

In one embodiment, as can be seen in Table 2 above, a SD or HD acts as a DSB Host and includes a DSB A Receptacle and/or a DSB B Plug. A PWH acting as a device can be connected to the SD or HD via a DSB B Receptacle present on the PWH and a DSB B Plug on the SD or HD. In such a connection, the DSB interface operates in USB mode and provides AVS capabilities from the SD or HD to the PWH.

The SD or HD can also act as a DSB Host to a FED without a cable. The FED without a cable connects to the SD or HD via a DSB B Receptacle present on the FED and a DSB Plug on the SD or HD. In such a connection, the DSB interface operates in the USB mode and provides software (SW) upgrade and AVS capabilities from the SD or HD to the FED.

Additionally, the SD or HD can act as a DSB Host to a FED with an integrated cable. The FED connects to the SD or HD via a DSB A Plug present on the integrated cable and a DSB A Receptacle on the SD or HD. In such a connection, the DSB interface operates in the USB mode and provides SW upgrade and AVS capabilities from the SD or HD to the FED.

In one embodiment, a PWH can act as a DSB Host and includes a DSB A Receptacle and/or a DSB B Plug. The PWH can act as a DSB Host to a FED without a cable. The FED without a cable connects to the PWH via a DSB B Receptacle present on the FED and a DSB B Plug on the PWH. In such a connection, the DSB interface operates in the USB mode and provides SW upgrade and AVS capabilities from the PWH to the FED.

Additionally, the PWH can act as a DSB Host to a FED with an integrated cable. The FED connects to the PWH via a DSB A Plug present on the integrated cable and a DSB A Receptacle on the PWH. In such a connection, the DSB interface operates in the USB mode and provides SW upgrade and AVS capabilities from the PWH to the FED.

In one embodiment, a PT can act as a DSB Host and includes a DSB A Receptacle and/or a DSB B Plug. The PT can act as a DSB Host to a FED without a cable. The FED without a cable connects to the PT via a DSB B Receptacle present on the FED and a DSB B Plug on the PT. In such a In one embodiment, the PT Charger acts as a DSB Host to a PT acting as a DSB Device. The PT connects to the PT Charger via a DSB A Receptacle present on the PT and a DSB A Plug on the PT Charger. In such a connection, the DSB interface operates in LPS mode and provides charging and SW upgrade capabilities from the PT Charger to the PT.

In one embodiment, incorrect connections are prevented by creating a generic connections scheme using the USB protocol for medical applications in which all host connectors are the same. Additionally, the parameter connectors are the same, although different from the host connectors. Another benefit of the DSB interface is caregivers can decrease or increase the number of parameters being monitored as a patient's acuity changes. This is accomplished simply by removing or plugging in more parameters, creating a "plug and play" environment.

In one embodiment, two illegal connections can be made and are described below with respect to two specific devices/hosts, but it should be understood by those of ordinary skill in the art that the same conditions are true with respect to misconnections between a generic host and a generic device.

By way of example, the first illegal connection is between any Patient Worn Hub (PWH) DSB Host receptacle and any Patient Worn Hub (PWH) DSB Device receptacle. The second is between the Parameter Transceiver (PT) DSB Host receptacle and Patient Worn Hub (PWH) DSB Device receptacle. Both of these illegal connections will be detected and handled through user notification on the Hosting Device. The connection between a PWH DSB Host receptacle and a PWH DSB Device receptacle is a DSB USB connection and the Host component will recognize the Device component is an illegal connection. The Host will then handle it appropriately, which, in one embodiment, includes displaying a message that the device is not supported as connected. The connection between a PT DSB Host and PWH DSB Device is a DSB LPS Host to a DSB USB Device connection. The DSB USB Device will not power up from a 3.3-Volt DSB LPS Host. The DSB LPS Host will sense a load current on and handle it appropriately, which in one embodiment, includes displaying a message that the device is not supported as connected.

In one embodiment, an additional DSB FED includes a system bridge in the form of a serial device interface. A third party parameter device connection is enabled through a device interface cable, which translates the output of the third party device to the protocol appropriate for use in the monitoring system. The device interface cable has a DSB connector at one end and a cable connector at the other end to interface with the host and the third party device respectively. The device interface cable is fully described in co-pending U.S. patent application Ser. No. (to be determined), entitled "Self-Contained Patient Monitor", filed on Nov. 18, 2011 and assigned to the Applicant of the present invention, which is incorporated by reference in its entirety as stated above.

In one embodiment, an additional DSB Device includes a bar code reader.

In one embodiment, an additional DSB device includes a Patient Worn Hub that acts both as a DSB host to a DSB device and as a device to a Smart Display (SD) host. In another embodiment, an additional DSB device includes a Patient Worn Hub that acts both as a DSB Host to a FED and as a device to a Headless Display (HD) host.

In most connections, communications and power are provided and additional power is negotiated between the DSB Host and DSB Device. In one embodiment, power control is implemented in the DSB Host. These functions are the same as in the USB standard with the addition of an auxiliary high power supply. In one embodiment, while the DSB interface is in the USB mode, USB 2.0 industry standards for electrical and software protocol compatibility is maintained while the mechanical interface is customized. In the USB mode, the DSB will support high-speed, full-speed, and low-speed data ranges. Not all data speed ranges are supported in all DSB applications.

In one embodiment, the USB physical interconnect is a tiered star topology and can function that way in the DSB. In one embodiment, the DSB interface is a two communications protocol interface capable of providing a single cable and a set of connectors with both USB and Low Power Serial (LPS) protocols to recognize and process whichever parameter is connected. From a power standpoint, however, USB operates at a relatively high power whereas serial can operate at lower power and therefore can be more cost effective. The DSB interface provides this benefit through the LPS protocol. In one embodiment, the USB physical interconnect is used in a one-to-one connection from a DSB Host to a DSB Device. Therefore, the DSB will utilize USB with a custom connector but alternately will implement a custom Low Power Serial (LPS) Interface. A DSB Host can support USB or LPS communication protocols but not both on a single port. In one embodiment, the LPS mode only supports a one-to-one connection from a DSB Host to a DSB FED. The LPS mode is primarily intended for use by a DSB Host that cannot support the USB Mode because it has limited power capabilities. Table 3 includes various embodiments of communication protocols used by a multitude of FED's.

TABLE 3

Devices Communications Protocols

| FED's | Communication Protocol |
| --- | --- |
| ECG/Resp | Dual (USB & LPS) |
| SpO₂ | Dual (USB & LPS) |
| Bridge | Dual (USB & LPS) |

TABLE 3-continued

Devices Communications Protocols

| FED's | Communication Protocol |
| --- | --- |
| 4 channel Invasive Pressure | USB |
| Single channel Invasive Pressure | USB |
| Cardiac Output | USB |
| End Tidal CO₂ | USB |
| Continuous Temperature | USB |
| SvO₂ | USB |
| BISx | USB |
| Multi-Gas | USB |
| Quick read temperature | USB |
| Bar Code reader | USB |
| EEG | USB |

When connected to a LPS DSB Host such as a Parameter Transceiver, the communication mode is LPS. When connected to a USB DSB Host such as a Patient Worn Hub or Smart Display, the communication mode is USB. The mode is determined by the FED based on the VBUS voltage supplied to it by the DSB Host.

In one embodiment, in the USB mode, VBUS power in managed per the USB 2.0 Standard. As mentioned above, the LPS mode is primarily intended to be used in a lower power application. It eliminates the need of a USB controller in a DSB Host, thereby saving considerable power in the DSB Host. There is also power savings in the FED since the USB interface is deactivated when the FED is in the LPS mode. In one embodiment, the LPS mode will limit the power it will supply to a Device to no more than 50 mA (165 mW). In one embodiment, in the LPS mode, a two wire interface using transistor-transistor logic (TTL) signal levels is used. In one embodiment, the LPS mode serial interface is based on the EIA232 (RS-232) Standard. The LPS mode will initially be implemented in the Parameter Transceiver. The first LPS FED's to be developed include ECG/Respiration, Bridge, and SpO₂.

In one embodiment, when a DSB device containing internal batteries is connected to a DSB host, the device can be charged and/or powered by the host. In one embodiment, when a DSB device without internal batteries is connected to a DSB host, the device can be powered by the host. In one embodiment, the DSB host contains a switched Auxiliary Voltage Supply (AVS) which can provide up to 15 W of power to DSB devices for battery charging or other high power needs. The AVS is a negotiated power supply and is supplied by the DSB host only when the DSB device requires it and the DSB host can provide it.

In one embodiment, when the Patient Worn Hub is connected to a Smart Display, the Smart Display acts as the DSB Host. In this configuration, the Patient Worn Hub can be charged by the Smart Display. An AVS present on the Smart Display can provide up to 15 Watts for battery charging or other high power needs from the Smart Display to a system device. In one embodiment, the Parameter Transceiver, though acting as a host, does not support AVS out since it has limited power capabilities. Devices that do not use AVS must be tolerant of 18-Volts on the AVS input.

In one embodiment, AVS is intended for, but not limited to, USB mode. Since LPS DSB Hosts have limited power capabilities, AVS is typically not provided in LPS mode. AVS is off until it is requested by a DSB Device and granted by the DSB Host. When AVS is active, VBUS is limited to 100 mA (One USB unit load). The DSB Device that requires AVS must be capable of operating on 100 mA (~500 mW) from VBUS until AVS is available at which time it will have up to 15 W of power to operate. DSB Host software identifies devices that require AVS power; in addition, the DSB Host performs all power budgeting tasks. Power must be requested and granted by the Host. In one embodiment, if the number of devices requiring AVS from a DSB Host exceeds the DSB Hosts power capability, then a system notification is initiated. If power is requested, but not available, a message is displayed indicating that the device connected exceeds power available for the system. In one embodiment, when AVS is turned on and the DSB Device is disconnected from the DSB Host, the DSB Host will turn off AVS. In one embodiment, when a DSB Device loses communications with a DSB Host, or, is reset for any reason, the DSB Host will turn off AVS.

In one embodiment, a DSB host and a DSB device are connected through a cable. In one embodiment, a component has a fixedly attached cable. DSB Devices can have attached cables of a fixed length and cable length cannot be extended. The length of these cables will be determined when the component is developed based on its intended use. A component with an attached fixed length cable may have two or more lengths. For example, in one embodiment, an IBP parameter measuring device includes a three meter cable for operating room (OR) use. In another embodiment, an IBP parameter measuring device includes a one meter cable for intensive care unit (ICU) use. These components attach directly to the DSB Host.

In one embodiment, components are interconnected with a detachable DSB cable. The detachable cable may be made in several lengths and has a different plug at each end.

The DSB cable is available in several lengths with a maximum length of approximately 5 meters, which is controlled by capacitance as per the USB specification.

In another embodiment, the DSB interface utilizes a zero length connection, which is a DSB Device docked directly with a DSB Host. The zero length connection is essentially a "B" plug attached to the DSB host.

In one embodiment, the DSB transfers signal and power over a shielded six-wire cable terminating in a six pin connector with mating shields. The signaling occurs over two wires. In one embodiment, the wires are named D+ and D− for the USB mode and the same wires are named RX and TX for the LPS mode. In the LPS mode, the baud rate is 921,600 baud, a requirement of the Parameter Transceiver.

In one embodiment, the cable also carries VBUS, AVS and GND to DSB Devices. VBUS is nominally +5 V at the source for USB and +3.3 V for LPS. Cable segments of variable lengths, up to several meters, are allowed. The appropriate conductor gauge is used to match the specified IR drop. AVS is a high power connection that provides up to 15 Watts from the DSB Host to the DSB Device. AVS is a switched supply and is off until it is requested by the DSB Device and granted by the DSB Host. If the DSB Host cannot provide AVS power to the requesting DSB Device a user notification is initiated. This occurs when a DSB Device requests AVS and the load would exceed the power that a DSB Host is able to supply. The DSB cable signal definitions and wire size for cable length, for one embodiment, are summarized in Tables 4 and 5.

In one embodiment, DSB devices with an attached fix length cable, which do not require auxiliary power or extra wires, do not contain AVS or spare wires within said attached fix length cable. Similarly, in one embodiment, DSB devices with an attached fix length cable, which require less than the maximum USB power, contain VBUS and GND wires within said attached fix length cable that are sized appropriately for the length of the cable used.

TABLE 4

Signal Definitions

| Signal Name | Signal | Minimum Sourced Current | AWG | Color | Comment |
|---|---|---|---|---|---|
| VBUS | +5 V/ +3.3 V | 500 mA | See Table 5 | Red | Mode Detect; +5 V = USB, +3.3 = LPS |
| D+/RX | Data | — | 28 | Green | D+ in USB Mode, RX in LPS Mode |
| D−/TX | Data | — | 28 | White | D− in USB Mode, TX in LPS Mode |
| GND | | 950 A* | See Table 5 | Black | Return for VBUS and SW-HV |
| AVS | +18 V | 850 mA | See Table 5 | Orange | Switched High Voltage, Up to 15 Watts |
| Shield | — | — | 40 | NA | >65% Tinned Copper Braided Shield and Aluminum Metalized Polyester Inner Shield with 28 AWG STC Drain Wire |
| Spare | TBD | — | 28 | Blue | Future use |

*When AVS is active VBUS is limited to 100 mA.

In one embodiment, the wire for VBUS is red and carries either 5 V or 3.3 V with a minimum sourced current of 500 mA. The VBUS is the mode detect signal and determines if the DSB interface operates on the USB protocol, providing 5 V of power, or the Low Power Serial (LPS) protocol, providing 3.3 V of power. When AVS is active, VBUS is limited to a sourced current of 100 mA.

In one embodiment, the two wires for data transmission are designated D+ in USB mode/RX in LPS mode and D− in USB mode/TX in LPS mode and are colored green and white respectively. Both data transmission wires are sized 28 American wire gauge (AWG).

In one embodiment, the wire for ground (GND) is black and carries the return for VBUS power and switched watt high voltage (SW-HV), with a minimum sourced current of 950 mA. When AVS is active, VBUS is limited to a sourced current of 100 mA and so the return for VBUS on the GND wire would be limited to a sourced current of 100 mA.

In one embodiment, the wire for AVS is orange and carries 18 V, providing a switched high voltage with up to 15 Watts and a minimum sourced current of 850 mA.

In one embodiment, shielding is sized 40 AWG and comprises >65% tinned copper braided shield and aluminum metalized polyester inner shield with 28 AWG drain wire.

In one embodiment, the DSB interface includes a spare wire sized 28 AWG that is colored blue and reserved for future use.

TABLE 5

Minimum Wire Size for Power Conductors in Detachable Cables

| Cable length (Meters) | VBUS Wire Size (AWG) | GND Wire Size (AWG) | AVS Wire Size (AWG) |
|---|---|---|---|
| 5 | 24 | 24 | 24 |
| 4 | 24 | 24 | 24 |
| 3 | 24 | 24 | 24 |
| 2 | 28 | 28 | 28 |
| 1 | 28 | 28 | 28 |
| 0.5 | 28 | 28 | 28 |

In one embodiment, as can be seen in Table 5 above, the wire size for the VBUS, GND, and AVS wires depends upon the length of the cable in meters. For 0.5, 1, and 2 meter long cables, the wire size for VBUS, GND, and AVS wires is 28 AWG. For 3, 4, and 5 meter long cables, the wire size for VBUS, GND, and AVS wires is 24 AWG.

The USB mode provides the 5-Volts power for VBUS and meets the USB standard for VBUS. In one embodiment, it also supports AVS.

In one embodiment, the ground wire is isolated from the shield within the cable but ground and shield are connected in the DSB Host. The shield is not intended to carry ground currents and therefore if the shield and ground need to be connected in a FED they should be connected through a low value resistor.

In one embodiment, the LPS can support standard baud rates from 300 to 921,600. In a preferred embodiment, the system will primarily use 921,600 baud to accommodate the Parameter Transceiver requirements and minimize complexity.

All DSB devices have an upstream connection. Upstream and downstream connectors are not mechanically interchangeable, thus eliminating illegal loop back connections at hubs. In one embodiment, the DSB cable has six conductors: a twisted signal pair of standard gauge, a spare conductor of 28 AWG, and a two power and a ground in a range of permitted gauges. In one embodiment, the connector is a seven-position connector with shielded housing, specified robustness, and ease of attach-detach characteristics. In one embodiment, the seven wire raw cable includes a woven braid and is shielded for robust applications, requiring only six conductors. In one embodiment, the DSB-A and DSB-B connector system shall provide for, and by design guarantee, connect sequencing as follows:

On connector insertion: the first connect is shield; the second connects are VBUS and GND; and the last connects are all remaining signals.

On connector removal: the first break is D+/RX, D−/TX, AVS, and Spare; the second breaks are VBUS and GND; and the last break is shield.

In one embodiment, the size of the DSB connectors is as follows: DSB-A Plug is approximately 12 W×5H×10 L mm; DSB-A Socket is approximately 14 W×7H×12 L mm; DSB-B Plug is approximately 10 W×8H×10 L mm; and DSB-B Socket is approximately 11 W×12H×12 L mm.

In one embodiment, in the USB mode, VBUS power in managed per the USB 2.0 Standard. In the LPS mode, VBUS is limited to 50 mA but can be turned off by the DSB Host. This may be done to conserve power in a FED if it is not to be used for a period of time or to force a FED hard reset.

In one embodiment, AVS is intended for, but not limited to, USB mode. Since LPS DSB Hosts have limited power capabilities, AVS is typically not provided in LPS mode. AVS is off until it is requested by a DSB Device and granted by the DSB Host. When AVS is active, VBUS is limited to 100 mA (One USB unit load). The interface requires that DSB devices must be capable of operating on 100 mA (~500 mW) from VBUS until AVS is available at which time it will have up to 15 W of power to operate. It is up to the DSB Host software to identify a device that requires AVS power. In one embodiment, if the number of devices requiring AVS from a DSB Host exceeds the DSB Hosts power capability, then a system notification is initiated, which, in one embodiment, is a message on the display that power limits have been exceeded. In one embodiment, when AVS is turned on and the Device is disconnected from the DSB Host, the DSB Host will turn off AVS. In one embodiment, when a DSB Device loses communications with a DSB Host, or, is reset for any reason, the DSB Host will turn off AVS.

In one embodiment, in the LPS mode, the Bus Protocol is a Spacelabs' proprietary protocol. In the LPS mode, the DSB Host is the Data Terminal Equipment (DTE) and the DSB Device is the Data Communications Equipment (DCE). The interconnect signal lines assume the names of the DSB Host. Therefore, on the DSB Host, TX is an output and RX is an input. On the FED, TX is connected to the RX input and RX is connected to the TX output.

In one embodiment, devices can be attached or removed at any time without having to turn off or cycle the power on any DSB Host or Device. In other words, all system components are hot pluggable.

The following section relates to the DSB Protocol Description. The DSB operates in two modes. In the USB mode, the protocol is the USB standard. When in the LPS mode the Spacelabs' LPS protocol is used.

In one embodiment, when a DSB device is connected to a USB DSB Host, it will have a USB Host software component. Any DSB device that is connected directly to the USB DSB Host with a DSB cable will utilize a USB device software component. The USB Host software component will identify the connection of the USB device and launch the appropriate USB driver. The USB DSB Host uses the Vendor Identification (VID) and Product Identification (PID) in the USB device to identify the appropriate driver. This software component is part of the operating system. It is subject to the requirements of the USB specification.

In one embodiment, the LPS protocol controls and enables the connection, communication, and data transfer between a DSB host and a DSB device. The LPS protocol is used to allow the most efficient use of power in a DSB Host. Minimizing the activity of the component that has the DSB host minimizes power use. The LPS provides a mechanism to support data rate/latency tradeoffs, congestion control, and data flow control. The protocol defines the rules governing the syntax, semantics, and synchronization of communication. It is implemented by a combination of hardware and software. At the lowest level, the protocol defines the behavior of a hardware connection.

In LPS mode, the DSB host controls the data flow, latency, and congestion. In one embodiment, the DSB host controls the data flow through a request/grant protocol. The DSB host dictates when the data from the DSB device can be sent and how much data can be sent. Available capacity up to the limit per DSB device will be granted to the requestor.

In LPS mode, the DSB device responds to the controls of the DSB host. In one embodiment, the device increases its data capacity through request for larger packet sizes. In one embodiment, the maximum packet size is a predefined limit. If the data capacity is not available and the requested data packet size is denied, the component has the responsibility to resolve the outcome. It is the responsibility of the device to manage and level the packet sizes from frame to frame. In one embodiment, all FEDs speak a common protocol language called the FED framework. The framework consists of numeric and waveform data packets where data can be compressed or decompressed. The FED and host must therefore agree on packet size. If a size is not supported, the FED must request a different packet size until an agreement is reached.

In one embodiment, the LPS protocol includes the following communications settings: a baud rate of 921,600; a data bit of 8; a parity of None; and stop bits equaling 1.

Data flow and congestion control are critical functions to maintain efficient control of wireless bandwidth and capacity for the DSB device. In one embodiment, components produce data at many different average rates and the DSB Host can have different data latency requirements. The DSB interface must be capable of supporting data through needs of the components. As a shared medium with a finite capacity, control must be in place to prevent undesired system wide reliability issues. In one embodiment, the packet request rate from the DSB host to the DSB device is the responsibility of the DSB host and is specified as 0.25 seconds. If the data volumes are irregular for each 0.25-second frame time there could be high variability in the data flow. In one embodiment, in the initialization packet, the DSB device includes a packet size request for future 0.25-second interval segments.

In various embodiments, the LPS protocol controls the powering of system components by the following on/off sequences. In one embodiment, the LPS initiates communications using the following protocols for power up sequence. In a first embodiment, the DSB host is off and the system follows the Start up sequence as listed below: 1) DSB Device connected to DSB Host; 2) DSB Host powers up if not already powered; 3) Device powers up with power from the DSB Host; 4) After a delay, the DSB Host sends packet request to Device; 5) Device sends identification/initialization packet; 6) DSB Host sends packet request to Device; 7) Device sends traffic packet. In a second embodiment, the DSB host is already on and the system follows the Start up sequence as follows (in this scenario, a DSB Host is operating and an additional parameter is connected): 1) Device plugged into DSB Host; 2) DSB Host detects the presence of Device; 3) After delay, DSB Host sends packet request to Device; 4) Device sends identification/initialization packet; 5) DSB Hosts send packet request to Device; 6) Device sends traffic packet.

In one embodiment, the LPS uses the following protocol for power down sequence. In a first embodiment, the DSB Host is on with one Device attached and the system follows the Power down sequence as follows: 1) Last Device unplugged from DSB Host; 2) DSB Host detects Device disconnect; 3) Device goes into predetermined state waiting for a DSB device to be connected.

In one embodiment, LPS Packets facilitate DSB LPS communications between a DSB Host and a DSB Device. The LPS Packets contain information necessary to control the LPS interface and are limited to DSB LPS.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is a three-dimensional illustration of one embodiment of a DSB A Connector 100 of a patient monitoring system. The DSB A Connector 100 will only accept the DSB A plug end of a DSB cable. DSB A Connectors (also known as Receptacles) are present on the monitor and other DSB host components of the patient monitoring system.

A common problem in operating and critical care settings in hospitals is liquid ingress into the sensors and connectors of monitoring systems, resulting in malfunction and damage to the system and time delay in restoring the system. In one embodiment, waterproof sealing of the sensors and connectors of the DSB system is achieved by incorporating a physical feature in the receptacle socket connector. Hence, even if the system falls into water, ingression is prevented and the system retains functionality. Waterproofing the system is accomplished by providing a double stage sealing over the receptacle socket outer surface. In one embodiment, the double stage sealing comprises a rectangular shaped washer with two raised ridges. Each ridge represents one stage of sealing. The washer and its ridges are fitted around the outside of the DSB A receptacle socket. This sealing prevents liquid ingress into the device. The double stage sealing enables the DSB connector system to meet the IPX4 protection level, allowing the system to be temporarily immersed in water for a short duration with no effect upon functionality. In addition, the system receives no physical damage while it is immersed in water for a short period of time. Therefore, inadvertent liquid spillage onto or temporary immersion of the DSB system in water will pose no danger to the operation of the system or safety of the patient.

Figure 2:
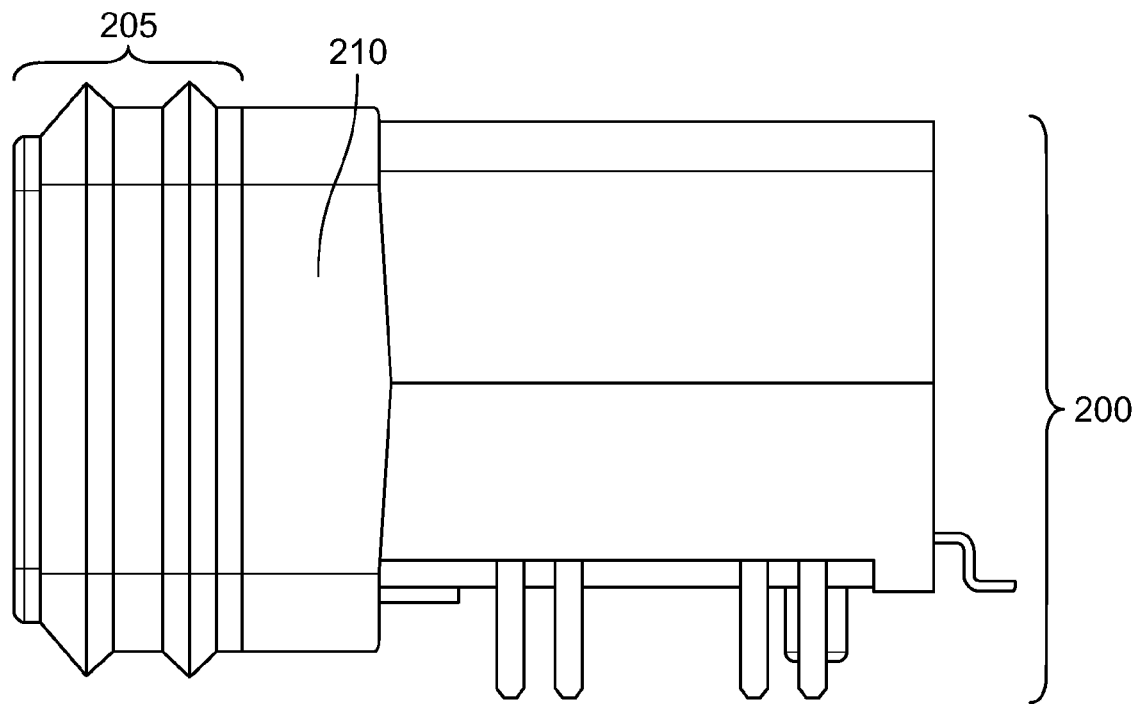
FIG. 2 is a side view illustration of one embodiment of a DSB A Connector of a patient monitoring system, depicting the double stage sealing present on the outer surface of the receptacle socket.

FIG. 2 is a side view illustration of one embodiment of a DSB A Connector 200 of a patient monitoring system, depicting the double stage sealing 205 present on the outer surface of the receptacle socket 210. The double stage sealing 205 acts to waterproof the junction between the connector body and the using assembly and meets the IPX4 protection level, allowing the component to be immersed temporarily in water without affecting functionality and causing no physical damage to the system.

Figure 3:
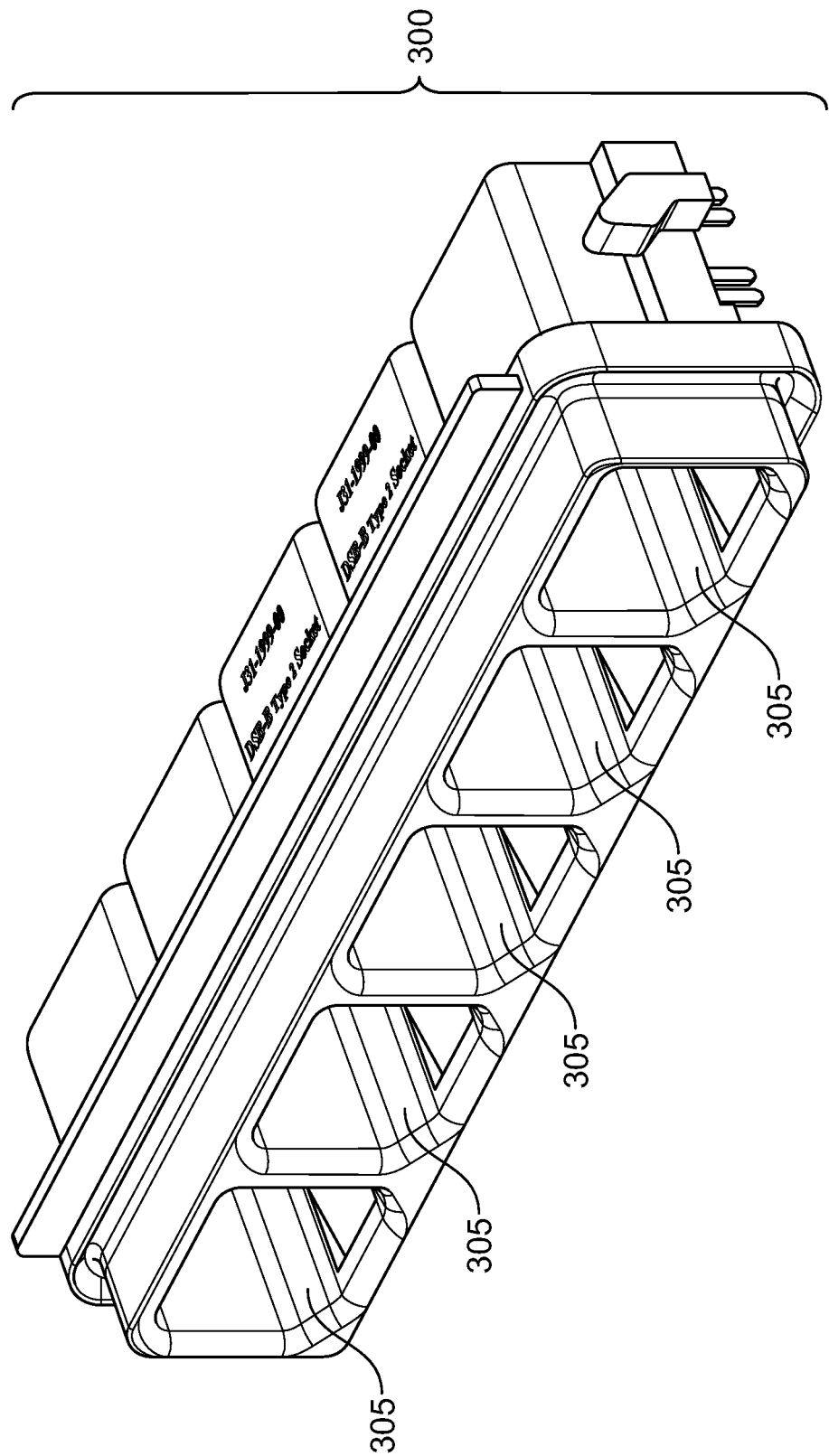
FIG. 3 is a three-dimensional illustration of one embodiment of a bank of five adjacent DSB A Connectors as would be found on the front of a monitor of a patient monitoring system.

FIG. 3 is a three-dimensional illustration of one embodiment of a bank 300 of five adjacent DSB A Connectors 305 as would be found on the front of a monitor of a patient monitoring system. These five DSB A Connectors 305 can receive DSB A plugs from DSB cables from up to five DSB devices (FEDs).

FIG. 4 is a three-dimensional illustration of one embodiment of a DSB B Connector 400 of the patient monitoring system. The DSB B Connector 400 will only accept the DSB B plug end of a DSB cable. DSB B Connectors (also known as Receptacles) are present on the DSB device components of the patient monitoring system.

FIG. 5A includes three-dimensional illustrations depicting the four types of connectors included in the DSB interface. The DSB interface comprises a set of series A connectors and a set of series B connectors. The series A connectors include a DSB A Plug 505 and a DSB A Receptacle 515. A DSB A Plug 505 extends from a DSB Device, either on an integrated cable or a DSB Cable, and is always oriented upstream toward the DSB Host. A DSB A Receptacle 515 is located on a DSB Host and provides downstream output from the DSB Host to a DSB Device. A DSB A Plug 505 is physically shaped to fit only into a DSB A Receptacle 515. In one embodiment, the DSB A Plug is formed in a wide and short rectangular shape. In other embodiments, the DSB A Plug takes the form of a larger rectangle, square, or any other shape that fits only into a matching DSB A Receptacle. The DSB A Receptacle is always shaped to accept only a matching DSB A Plug.

The series B connectors include a DSB B Plug 510 and a DSB B Receptacle 520. A DSB B Plug 510 extends from a DSB Host, either on an integrated cable or a DSB Cable, and is always oriented downstream toward the DSB Device. A DSB B Receptacle 510 is located on a DSB Device and provides upstream input to the DSB Device from the DSB Host. A DSB B Plug 510 is physically shaped to fit only into a DSB B Receptacle 520. In one embodiment, the DSB B Plug is formed in a narrow rectangular shape with an outwardly curved bottom edge. In other embodiments, the DSB B Plug takes the form of a wider rectangle, square, or any other shape that fits only into a matching DSB Receptacle. The DSB B Receptacle is always shaped to accept only a matching DSB B Plug.

Figure 5B:
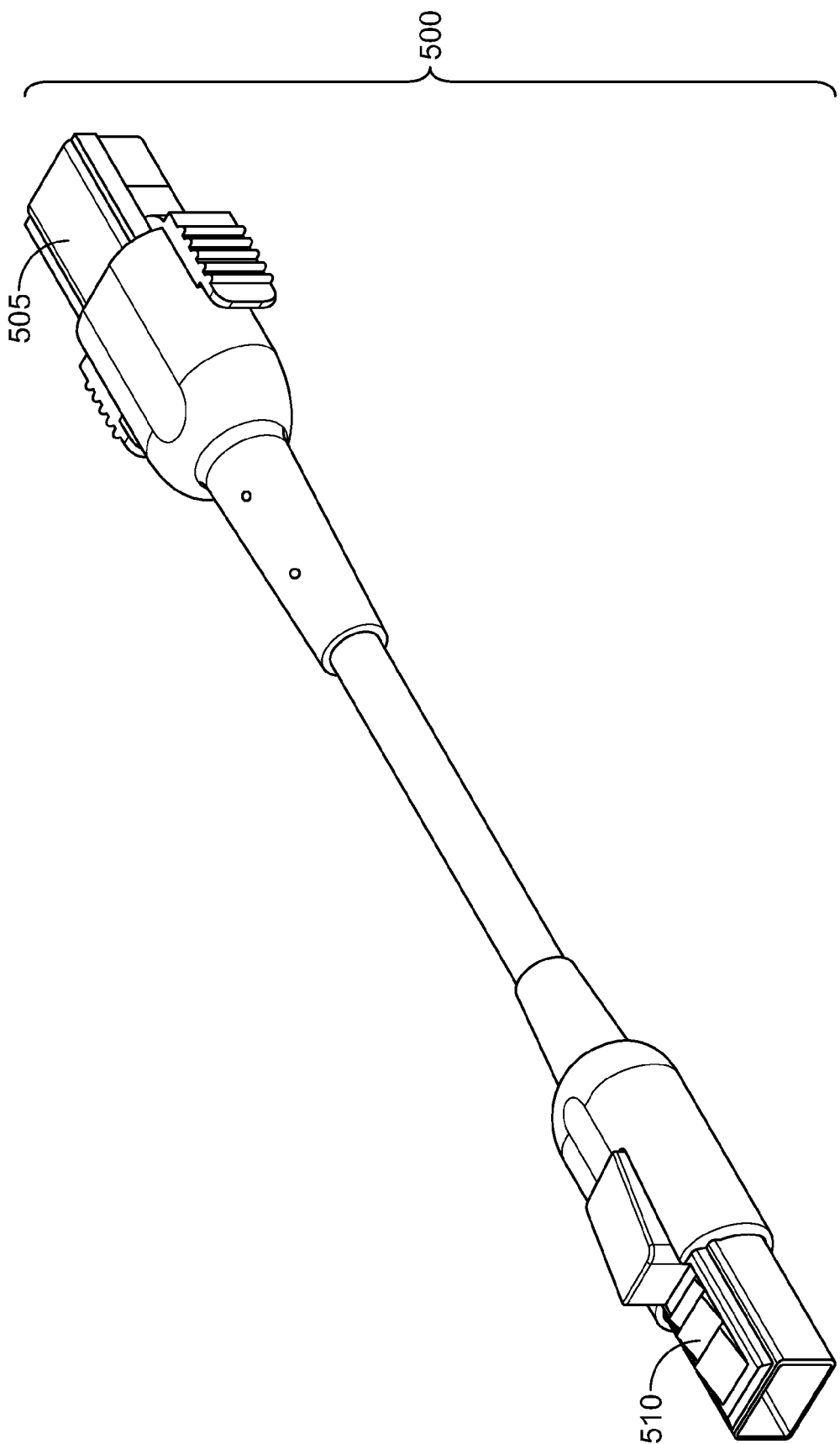
FIG. 5B is a three-dimensional illustration of one embodiment of a DSB cable of a patient monitoring system.

FIG. 5B is a three-dimensional illustration of one embodiment of a DSB Cable 500 of a patient monitoring system. The DSB A plug end 505 can only be plugged into a DSB A Connector and the DSB B plug end 510 can only be plugged into a DSB B Connector. The DSB cable acts to provide communications and power transfer between DSB hosts and devices of the patient monitoring system. Hosts and devices have the ability to communicate with one another but only DSB hosts can provide DSB devices with power. The DSB Cable allows for transmission through the industry standard USB protocol and the Spacelabs Healthcare proprietary LPS protocol. In one embodiment, lower powered devices are able to receive power from a host via the LPS protocol. In one embodiment, the host contains an Auxiliary Voltage Supply (AVS) and has the ability to deliver and negotiate higher power transfers, up to 15 W, to devices with greater power needs.

Figure 6:
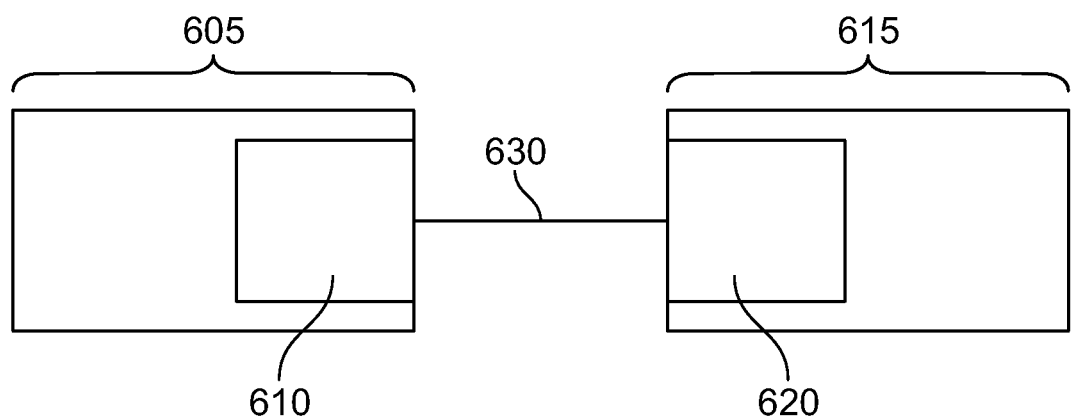
FIG. 6 is a block diagram depicting one embodiment of a component representing a DSB host connected via a DSB cable to a component representing a DSB device.

FIG. 6 is a block diagram depicting one embodiment of a component 605 representing a DSB host with an "A" type receptacle 610 connected via a DSB Cable 630 to a component 615 representing a DSB device with a "B" type connector 620. In one embodiment, the patient monitoring system contains a DSB host and a multitude of other components, each of these others being DSB devices. In another embodiment, a single component is both a DSB host and a DSB device. In another embodiment, the patient monitoring system contains a DSB host, a first multitude of other components, each of these others being a DSB host and a DSB device, and a second multitude of other components, each of these others being only a DSB device.

Figure 7:
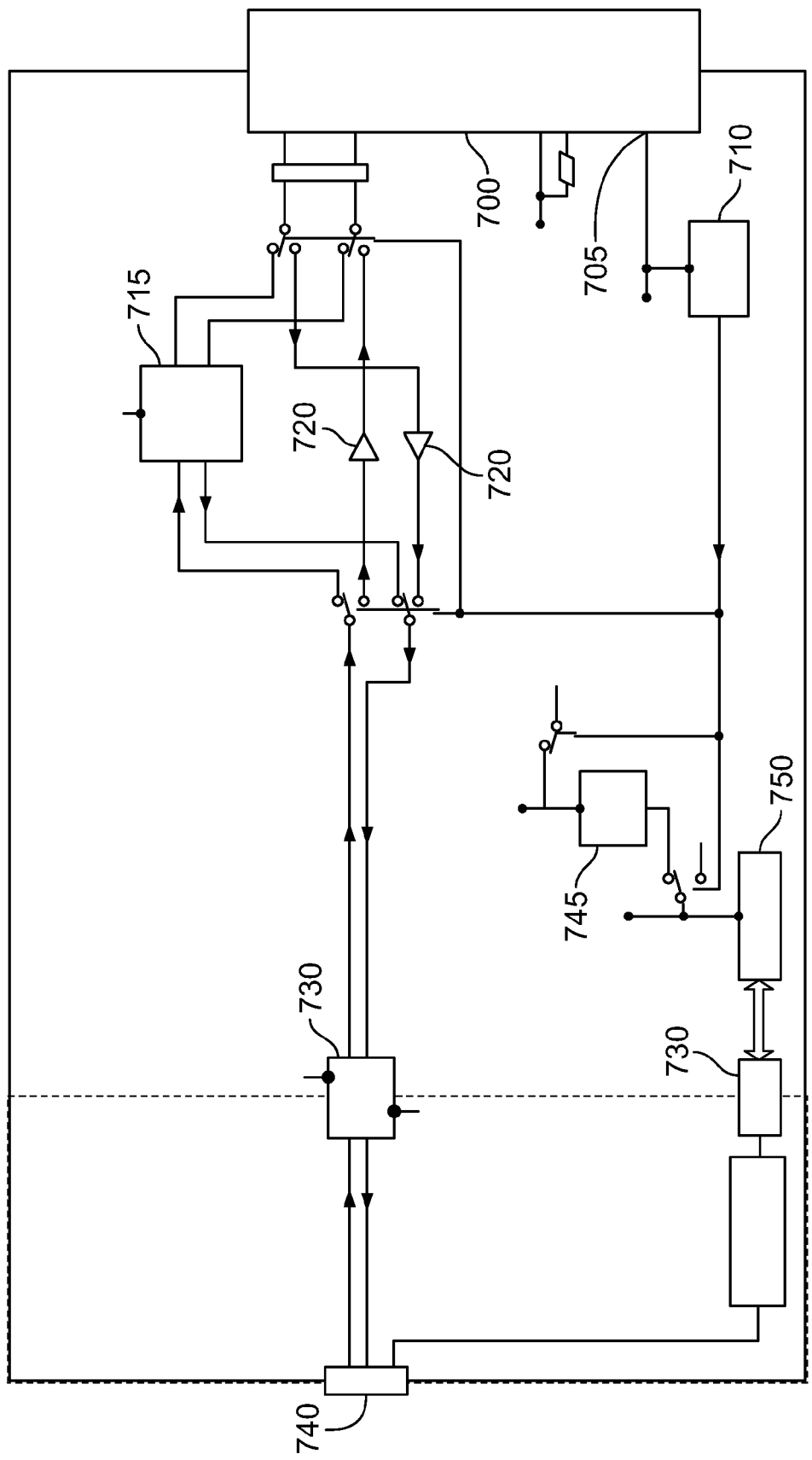
FIG. 7 is an illustration of one embodiment of the generalized DSB interface of a patient monitoring system which incorporates both the USB interface and the LPS interface.

FIG. 7 is an illustration of one embodiment of the generalized DSB interface of the patient monitoring system which incorporates both the USB interface and the LPS interface. The figure shows one embodiment of the generalized interface for the DSB as used in a multitude of Front End Devices (FED). The USB standard provides for a 5V power supply to be present on the interface. Implementation of the LPS interface uses a 3V power supply. A comparator circuit is used to sense the applied voltage and switch a set of electronic switches to configure the interface appropriately. This device is labeled as "Mode Detection" 710. The USB/Serial Bridge 715 is the USB interface circuitry. The Buffers 720 provide the asynchronous serial interface.

Two devices 730, 735 provide isolation between the DSB Host 700 and the DSB Device 740. Device 730 provides isolation for the digital communications signals. Device 735 provides isolated power to the DSB Device 740. This interface method is developed primarily for a patient applied device. In one embodiment, the DSB Device 740 measures ECG. In another embodiment, the DSB Device 740 measures SpO$_2$.

The DSB Device 740 then can receive asynchronous signals direct from a LPS host or via a USB Host. The power difference between the USB and serial Host is accommodated by the power switching on the 3.3V LDO (Low Dropout Regulator) 745 and the Power Converter 750. When running from a 3.3V serial host the power is supplied directly. When running off the 5V host the 3.3V LDO 745 is used to regulate the 5V to 3.3V to the power converter 750. Thus, the power converter 750 sees 3.3V in either case.

Figure 8:
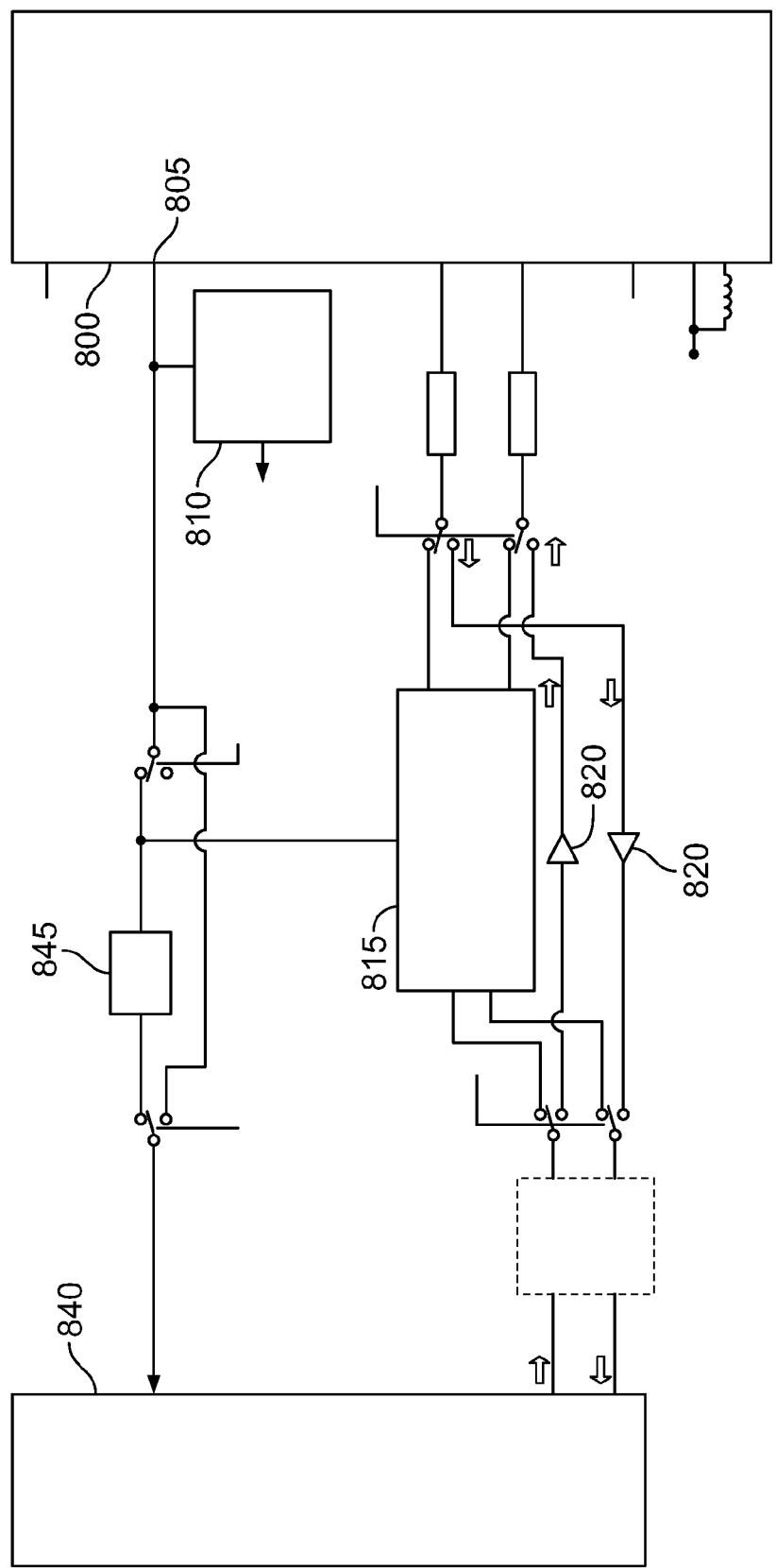
FIG. 8 is an illustration of another embodiment of the generalized DSB interface of a patient monitoring system.

FIG. 8 is an illustration of another embodiment of the generalized DSB interface of a patient monitoring system. The figure shows another embodiment of the generalized interface for the DSB as used in a multitude of Front End Devices (FED). The USB standard provides for a 5V power supply to be present on the interface. Implementation of the LPS interface uses a 3V power supply. A comparator circuit is used to sense the applied voltage and switch a set of electronic switches to configure the interface appropriately. This device is labeled as "Mode Detection" 810. The USB/Serial Bridge 815 is the USB interface circuitry. The buffers 820 provide the asynchronous serial interface. The DSB Device 840 then can receive asynchronous signals direct from a 3V host or via a USB interface Host. In one embodiment, the DSB Device 840 is a Serial Device Interface. The power difference between the USB and serial Host is accommodated by the power switching on the 3.3V LDO (Low Dropout Regulator) 845. When running from a 3.3V serial host the power is supplied directly. When running off the 5V host the 3.3V LDO 845 is used to regulate the 5V to 3.3V.

Figure 9:
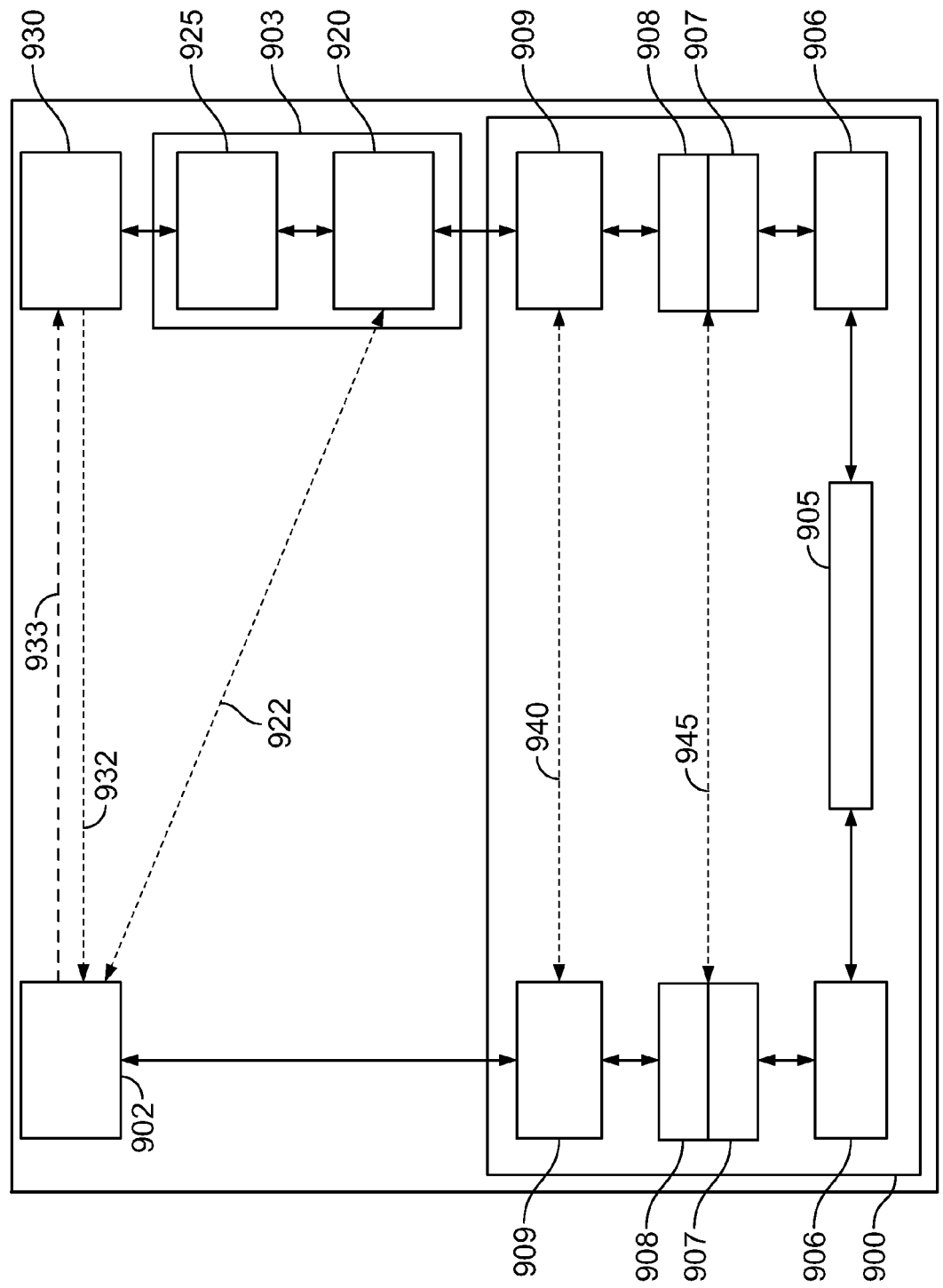
FIG. 9 is a flow chart illustration of one embodiment of the physical relationships within the DSB LPS Mode protocol stack.

FIG. 9 is a flow chart illustration of one embodiment of the physical relationships within the DSB LPS Mode Protocol Stack. The DSB LPS 900 communicates with both the FED/DSB Device 902 and the DSB Host 903. Within the DSB LPS 900, the LPS Mode 905 communicates with a universal asynchronous receiver/transmitter (UART) 906 on both sides of the interface. Both UART's 906 then communicate with a media access controller (MAC) 907 and Error Handling 908, again on both sides of the interface. Signals then pass to the Flow Control 909 on both sides. On the device side, the Flow Control 909 communicates with the FED/DSB Device 902. On the host side, the Flow Control 909 communicates with the DSB Host 903. Within the DSB Host 903, the Parameter Transceiver 920 communicates with the AP 925. The AP 925 then communicates with the FED Host 930, which in turn controls 932 the FED/DSB Device 902. The FED/DSB Device 902 delivers waveform and numeric data 933 to the FED Host 930 and is also able to communicate 922 with the Parameter Transceiver 920. Within the DSB LPS 900, flow control 940 also exists between the two Flow Control 909 ends of the interface. In addition, a data link 945 exists between the MAC 907 and Error Handling 908 portions of the two sides of the DSB LPS 900 interface.

Figure 10:
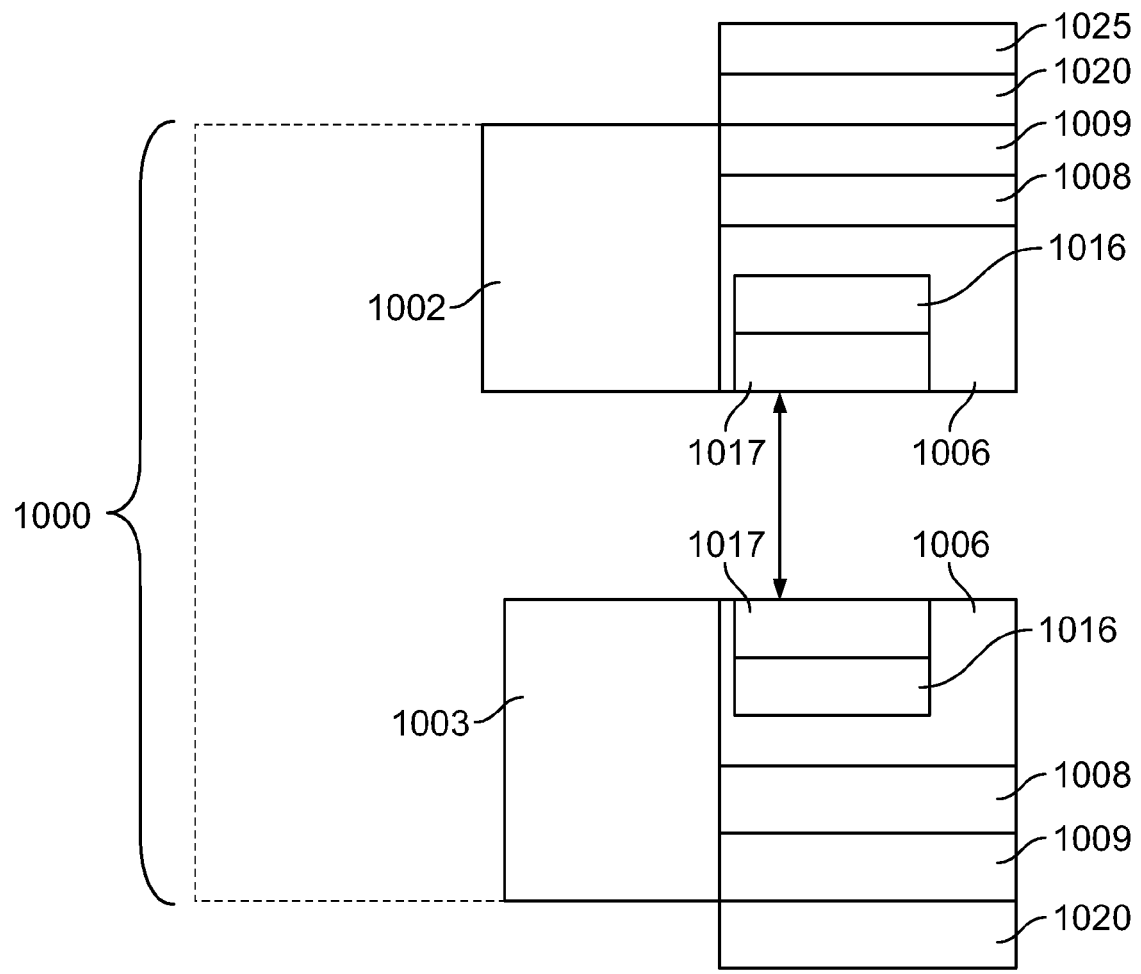
FIG. 10 is an illustration of one embodiment of an overview of the DSB LPS Mode protocol stack; and, FIG. 11 is an illustration depicting various embodiments of exemplary interconnections between components of a patient monitoring system utilizing the DSB Interface.

FIG. 10 is an illustration of one embodiment of an overview of the DSB LPS Mode Protocol Stack. Both the DSB host 1003 and the DSB device 1002 contain a UART 1006 with a datalink 1016 and a physical connector 1017, where the two components are attached by a DSB cable or are mounted to one another. After the UART 1006, both components then have a DSB LPS Datalink 1008 and then a DSB LPS Transport 1009, all within the DSB LPS 1000 interface between the two. Beyond the DSB LPS 1000 interface, both components have an application driver 1020 and the DSB device 3182 also includes the Parameter 1025.

Figure 11:
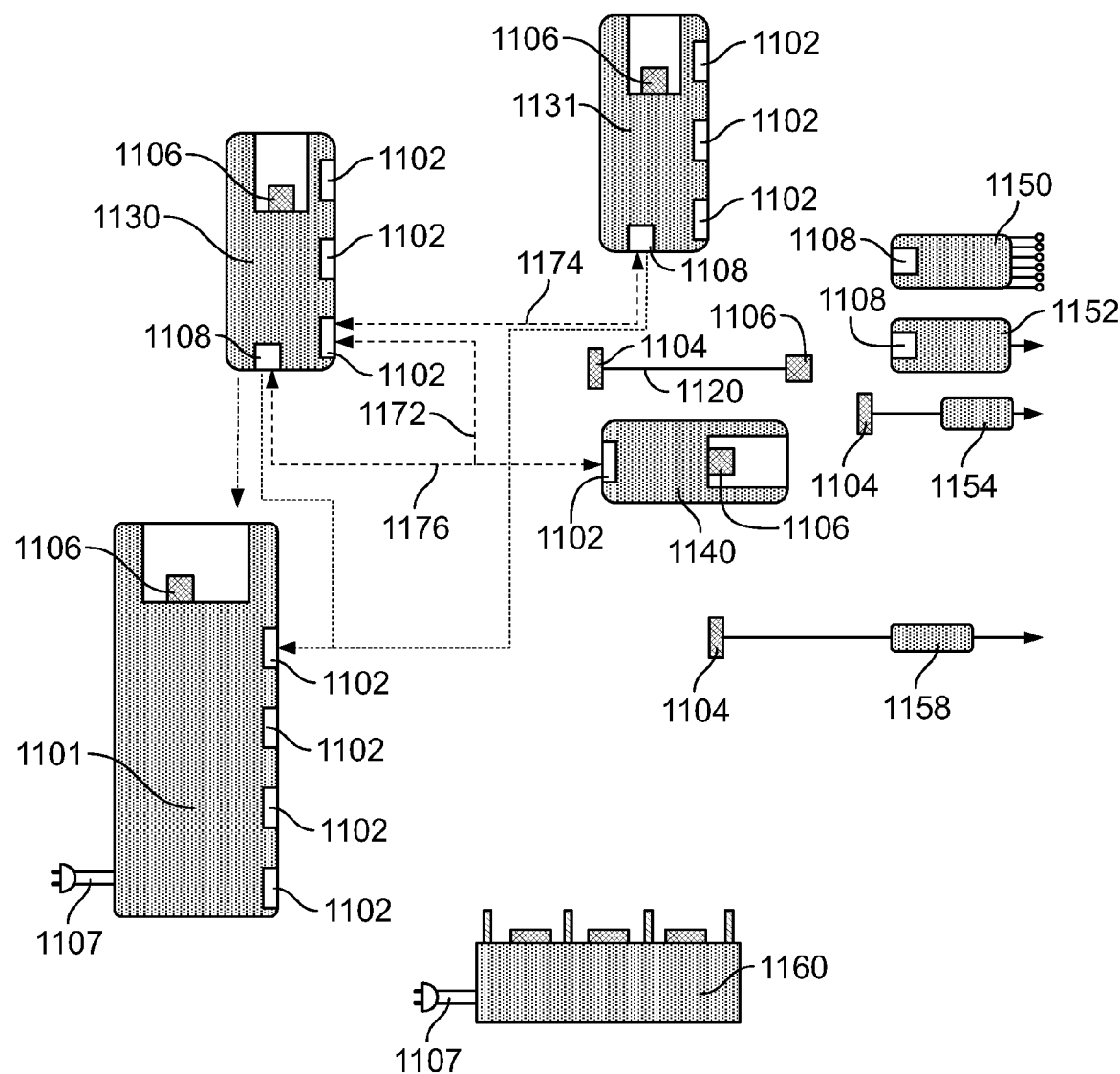

FIG. 11 is an illustration depicting various embodiments of exemplary interconnections between components of a patient monitoring system utilizing the DSB interface. In this embodiment, a Smart Display (SD) or Headless Display (HD) 1101 is pictured containing four DSB A Receptacles 1102, a docking port with a DSB B plug 1106, and a power plug 1107. A Patient Worn Hub 1130 is pictured above the Display 1101 and contains three DSB A Receptacles 1102, one DSB B plug 1106, and one DSB B Receptacle 1108. The Patient Worn Hub can act both as a DSB Host and as a DSB Device. In one embodiment, the Patient Worn Hub 1130 can dock with the Display 1101 via its DSB B Receptacle 1108 and the DSB B plug 1106 present on the Display 1101. In another embodiment, a device can be plugged into the Patient Worn Hub 1130 so it can be used to measure patient physiological data. A Parameter Transceiver 1140 is pictured in the center of the figure. The Parameter Transceiver contains one DSB A Receptacle 1102 and one DSB B plug 1106. Above the Parameter Transceiver is a DSB cable 1120, with a DSB A plug 1104 and a DSB B plug 1106 at either ends. To the right are three LPS Front End Devices: an ECG/Respiration measurement device 1150, containing one DSB B Receptacle 1108; a Bridge device 1152, also containing one DSB B Receptacle 1108; and, an $SpO_2$ measuring device 1154, containing an attached fixed cable with a DSB A plug 1104. Below these devices is pictured another Front End Device 1158. This Front End Device 1158 also includes an attached fix cable with a DSB A plug 1104. In various embodiments, this Front End Device 1158 can be used to measure any patient physiological data including but not limited to: 4 channel invasive pressure; single channel invasive pressure; cardiac output; end tidal $CO_2$; continuous temperature (YSI); $SvO_2$; BISx; multi-gas; quick read temperature (tympanic); bar code reader; EEG; and, other future physiological measurements. At the bottom of the figure is pictured a charger base 1160 for Parameter Transceivers, including its own power plug 1107.

FIG. 11 also illustrates three possible illegal connections within the system. Two of these are Patient Worn Hub—Patient Worn Hub and the other is Patient Worn Hub—Parameter Transceiver. The first illegal connection 1172 occurs when a DSB cable's DSB B plug is plugged into a Patient Worn Hub's 1130 DSB B Receptacle 1108 and the DSB A plug at the other end of the cable is plugged into the DSB A Receptacle 1102 on the same Patient Worn Hub 1130, essentially plugging the Patient Worn Hub 1130 into itself. The second illegal connection 1174 occurs when the DSB A plug of a DSB cable is plugged into the DSB A Receptacle 1102 of one Patient Worn Hub 1130 and the DSB B plug at the other end of the cable is plugged into the DSB B Receptacle 1108 of another Patient Worn Hub 1131. The third illegal connection 1176 occurs when the DSB B plug of a DSB cable is plugged into the DSB B Receptacle 1108 of a Patient Worn Hub 1130 and the DSB A plug at the other end of the cable is plugged into the DSB A Receptacle 1102 of a Parameter Transceiver 1140. The illegal connections are detected and handled through user notification on the Hosting Device.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A dual serial bus(DSB) communication and power interface system for electronic components, capable of operating in a first serial protocol and a second serial protocol, comprising a physical cable between said components, wherein said physical cable contains at least six separate conductors and wherein said at least six separate conductors comprise:

A first conductor, wherein said first conductor is a virtual bus (VBUS) conductor and transfers power from a first electronic component to a second electronic component and wherein the first conductor is adapted to transfer 5V of power when operating in the first serial protocol and transfer 3.3V of power when operating in the second serial protocol;

A second conductor, wherein said second conductor is a data transmitting conductor and sends data from said first electronic component to said second electronic component;

A third conductor, wherein said third conductor is a data receiving conductor and receives data to said first electronic component sent from said second electronic component;

A third conductor, wherein said third conductor is a data receiving conductor and receives data to said first electronic component sent from said second electronic component;

A fourth conductor, wherein said fourth conductor is a ground(GND) conductor and receives return power to said first electronic component transferred from said second electronic component;

A fifth conductor, wherein said fifth conductor is an auxiliary voltage supply(AVS) conductor and is adapted to transfer higher amounts of power from said first electronic component to said second electronic component than is capable of being transferred by said first conductor while said first conductor is transferring power in accordance with the first or second serial protocol; and, A sixth conductor, wherein said sixth conductor is a spare conductor.

2. The dual serial bus communication and power interface system of claim 1, wherein said interface is used to communicate and distribute power between components of a patient monitoring system.

3. The dual serial bus communication and power interface system of claim 1, wherein each component is designated as a dual serial bus (DSB) Host, DSB Device, or, both a DSB Host and DSB Device.

4. The dual serial bus communication and power interface system of claim 3, wherein a DSB Host is in bi-directional communication with a connected DSB Device, can supply operating and battery charging power to the connected DSB Device, and can control the connected DSB Device.

5. The dual serial bus communication and power interface system of claim 3, wherein a DSB Host contains a switched Auxiliary Voltage Supply (AVS) which can provide up to 15 W of power to attached DSB Devices.

6. The dual serial bus communication and power interface system of claim 5, wherein the AVS power must be requested by a DSB Device and granted by the DSB Host.

7. The dual serial bus communication and power interface system of claim 3, wherein a DSB Host comprises any one of a Patient Worn Hub (PWH), Smart Display (SD), Headless Display (HD), Network Computer (NC), or, Parameter Transceiver (PT).

8. The dual serial bus communication and power interface system of claim 3, wherein a DSB Device comprises at least one of a ECG/respiration in 3-lead, 5-lead, 6-lead, and 10-lead configurations, $SpO_2$ sensor, invasive blood pressure (IBP) 4 channel adapter and single channel connection, cardiac output sensor, end tidal $CO_2$ sensor, continuous temperature sensor, $SvO_2$ sensor, bispectral index (BISx) sensor, multi-gas sensor, tympanic temperature sensor, or EEG sensor.

9. The dual serial bus communication and power interface system for electronic components of claim 3, wherein a Patient Worn Hub (PWH) functions both as a DSB Host and a DSB Device.

10. The dual serial bus communication and power interface system for electronic components of claim 3, wherein each DSB Host contains at least one DSB-A type receptacle which accepts only a DSB-A type plug and/or at least one integrated cable with a DSB-B type plug at the end of said cable and, each DSB Device contains at least one DSB-B type receptacle which accepts only a DSB-B type plug and/or at least one integrated cable with a DSB-A type plug at the end of said cable.

11. The dual serial bus communication and power interface system for electronic components of claim 10, wherein each DSB-A type receptacle and DSB-B type receptacle comprises a double stage sealing over the receptacle socket outer surface to prevent liquid ingress at the point of connection.

12. The dual serial bus communication and power interface system of claim 3, wherein a DSB Device is docked directly with a DSB Host, connected to a DSB Host via a fixedly attached cable, or connected to a DSB Host via a detachable DSB cable, wherein each detachable DSB cable contains a DSB-A type plug on one end and a DSB-B type plug on the other end.

13. The dual serial bus communication and power interface system for electronic components of claim 12, wherein, said fixedly attached cable and said detachable DSB cable transfer signal and power over a shielded multi-wire cable terminating in a connector with mating shields.

14. The dual serial bus communication and power interface system for electronic components of claim 4, wherein the VBUS voltage present on a DSB Host device determines whether the DSB Device operates in a USB mode or a LPS mode.

\* \* \* \* \*